United States Patent [19]

Castonguay

[11] Patent Number: 5,615,294
[45] Date of Patent: Mar. 25, 1997

[54] APPARATUS FOR COLLECTING LIGHT AND ITS METHOD OF MANUFACTURE

[75] Inventor: Raymond J. Castonguay, Tucson, Ariz.

[73] Assignee: Breault Research Organization, Tucson, Ariz.

[21] Appl. No.: 479,663

[22] Filed: Jun. 7, 1995

Related U.S. Application Data

[62] Division of Ser. No. 230,546, Apr. 20, 1994, Pat. No. 5,475,617, which is a division of Ser. No. 983,470, Nov. 30, 1992, Pat. No. 5,313,542.

[51] Int. Cl.⁶ ........................................................ G02B 6/04
[52] U.S. Cl. .................................................. 385/115; 385/121
[58] Field of Search ..................................... 385/115, 116, 385/120, 121

[56] References Cited

U.S. PATENT DOCUMENTS

| | | | |
|---|---|---|---|
| 2,354,591 | 7/1944 | Goldsmith | 178/7.5 |
| 3,033,071 | 5/1962 | Hicks, Jr. | 385/116 |
| 4,128,760 | 12/1978 | Del Signore, II | 250/214 B |
| 4,202,599 | 5/1980 | Tosswill | 385/120 |
| 4,243,879 | 1/1981 | Carroll et al. | 250/221 |
| 4,360,275 | 11/1982 | Louderback | 356/446 |
| 4,390,277 | 6/1983 | Quinn | 356/371 |
| 4,573,082 | 2/1986 | Jeskey | 385/120 X |
| 4,645,920 | 2/1987 | Carroll et al. | 250/221 |
| 4,710,642 | 12/1987 | McNeil | 250/571 |
| 4,843,565 | 6/1989 | Rose | 364/513 |
| 4,904,049 | 2/1990 | Hegg | 385/120 |
| 4,914,284 | 4/1990 | Halldorsson et al. | 250/206.2 |
| 4,954,962 | 9/1990 | Evans, Jr. et al. | 364/513 |
| 4,991,971 | 2/1991 | Geary et al. | 356/446 |
| 4,993,826 | 2/1991 | Yoder, Jr. | 351/212 |
| 4,998,819 | 3/1991 | Labinger et al. | 351/212 |
| 5,015,840 | 5/1991 | Blau | 250/221 |
| 5,032,023 | 7/1991 | Schneiter | 356/3.05 |
| 5,125,064 | 6/1992 | Naselli et al. | 385/116 |
| 5,134,680 | 7/1992 | Schempp | 385/116 |
| 5,286,967 | 2/1994 | Bates | 250/205 |
| 5,303,373 | 4/1994 | Harootian, Jr. | 385/115 |
| 5,313,542 | 5/1994 | Castonguay | 385/115 |
| 5,392,125 | 2/1995 | Reisser | 356/445 |
| 5,475,617 | 12/1995 | Castonguay | 364/525 |

FOREIGN PATENT DOCUMENTS 52-40146 3/1977 Japan ........................................ 385/121

Primary Examiner—John D. Lee
Attorney, Agent, or Firm—Donald J. Lisa

[57] ABSTRACT

A portable scatterometer and/or an angular radiated light measurement instrument that uses a measurement head which includes a double tapered fiber optic bundle with a concave front face to simultaneously collect partial or full hemispherically scattered light reflected from a point on a surface illuminated by a depolarized, telescopically focused, laser diode source, the light rays being received by each fiber normal to its face. The image of the collected light beams is minified and coupled by the fiber optic bundle into an anti-blooming CID camera with an x-y scanning area array which converts the light beams to electrical signals. In a unique real time, 486-computer-controlled, data acquisition and reconstruction process, a frame grabber and a unique algorithm are used to collect over 200,000 points of light, reconstruct the data into a 2D or 3D scatter profile, and display the results, all within one second. Multiple embodiments of the tapered fiber optic bundle collector include a full hemispherical version with the laser source directed through the boule, a unitary boule fused from two tapered halves, a linear in-plane tapered bundle and a partial taper with imaging lens mode. Alignment mechanisms provide z-translation, azimuth, and focus adjustments. The measurement unit is in a compact, rugged aluminum housing which is adapted to be secured to a production line machine for a variety of services, such as, a quality control inspection device.

21 Claims, 14 Drawing Sheets

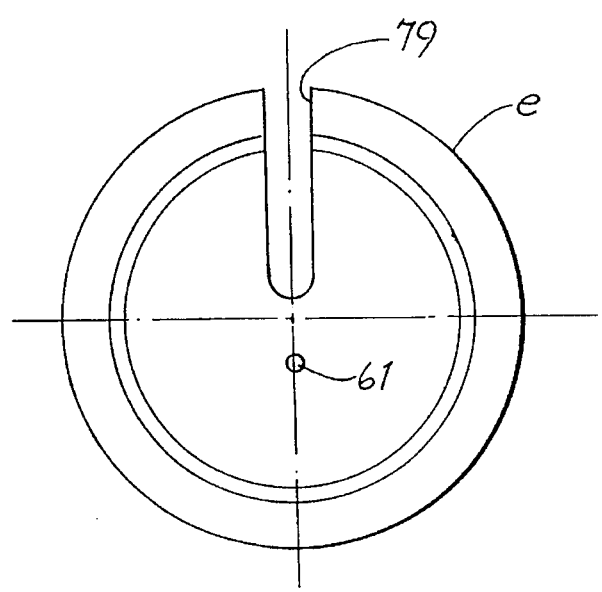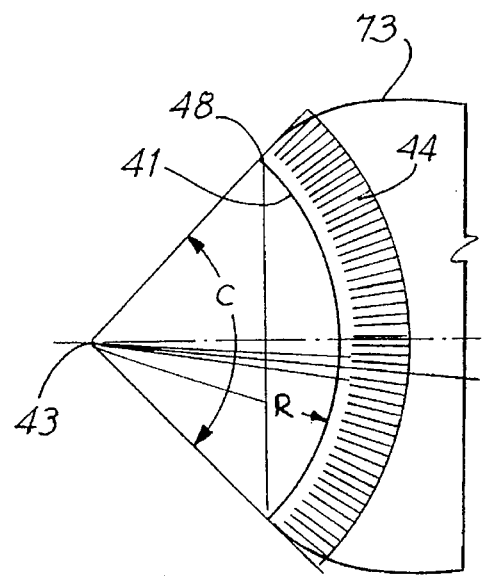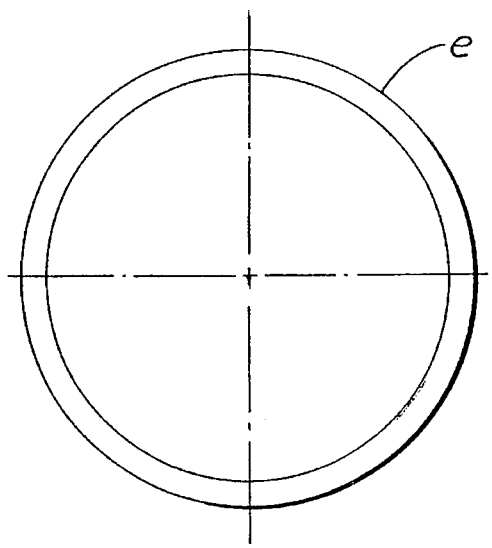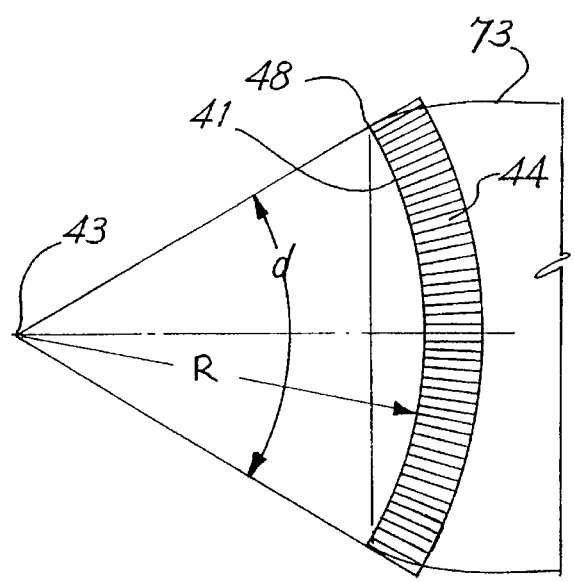
Fig. 7B    Fig. 10
Fig. 11B   Fig. 11A

APPARATUS FOR COLLECTING LIGHT AND ITS METHOD OF MANUFACTURE

This application is a division of application Ser. No. 08/230,546 filed Apr. 20, 1994 now U.S. Pat. No. 5,475,617 issued Dec. 12, 1995 which is a division of original application Ser. No. 07/983,470 filed Nov. 30, 1992 now U.S. Pat. No. 5,313,542 issued May 17, 1994.

BACKGROUND OF THE INVENTION

1. Fields of the Invention

The present invention relates generally to an apparatus and method of measuring hemispherical light scattered or emitted from a source, and, more particularly, to a portable scatterometer which uses a double tapered fiber optic bundle with a concave spherical face, a CID camera, and a frame grabber to hemispherically collect scattered light reflected from a laser illuminated sample and a unique algorithm to rapidly reconstruct the scatter profile on a computer screen.

2. Discussion of Background and Prior Art a. Scatterometers

Scatter from optical components reduces signal power, limits resolution, produces noise and has appeared as an unexpected problem in more than one optical design. Stover, "Optical Scatter: Careful Measurement Of Optical Scatter Provides A Keen Diagnostic", *Lasers & Optronics*, August 1988.

Optical designers and manufacturers require a precise and fast hemispherical light scatter measurement tool because many optical surfaces interact with light in unpredictable ways.

A scatterometer is a widely used and extremely valuable tool for optical designers, measuring scattered light from test objects in order to determine the quality and characteristics of surfaces down to the angstrom level.

In 1987 Breault Research Organization, Inc. ("BRO") introduced a multi-wavelength, surface-scanning, fully automated scatterometer ("FASCAT 360") system for use in research and development markets. The system could accommodate up to seven lasers and obtained full hemispherical measurements of the light reflected from or transmitted through a sample, but, only by rotating a photosensitive detector 360 degrees about the sample holder while allowing for three-axis (X,Y and Z) rotation and translation of the sample itself (all automated). The instrument is a Bi-Directional Reflectometer ("BDR") capable of measuring BiDirectional Reflectance Distribution Functions ("BRDF") and BiDirectional Transmittance Functions ("BTDF") both in-plane and out-of-plane. The system printed 2-D and 3-D plots of the data in real time and provided unparalleled versatility and dependability.

Until recently, this now conventional technology has limited the range of applications of scatterometers because of its large size (a 4'×8' steel top table completely encased in a Center For Radiological Devices and Health Class 1 housing, called the "truck", with sample access through safety interlock doors and a 386SX computer/laser printer system), its high cost ($400,000–$600,000) and its long acquisition time (10 minutes to 3 hours to measure, calculate and print a complete analysis of a sample).

To overcome this size and cost disadvantage, in 1988 Toomay, Mathis & Associates, Inc. ("TMA") introduced a single laser, table mounted, Complete Angle Scatter Instrument ("CASI"™) Class 3 scatterometer, but at great sacrifice to versatility and dependability. While this instrument provided three axis rotation and translation (one of which was automated) of the sample and 360 degree "sweep" (a different technique than 360 degree rotation about the sample used by FASCAT) of the detector, it could only provide 2-D plots of BSDF and still was relatively expensive ($97,000–$166,000).

Even more recently, still lower cost, hand-held, battery-powered, microprocessor-controlled scatterometers have been introduced using hand-held or bench-mounted measurement heads with up to 8 individual, non-movable detectors spaced about the sample which restricted versatility even more and which further sacrificed reliability and volume of data. While performing some useful function, these smaller units are restricted in that they assume the surface to be measured is homogeneous and that there is no interaction of light which prevents homogeneity. Thus, they are restricted in the number of measurements they can make.

The above attempts to design smaller instruments led to instruments that had much less capability than full scale versions, and, as a result, important information was lost. Applicant has found a solution to this problem which minimizes the sacrifices made in capability to achieve the small size and yet can measure scattered light on un-nice, non-behaved, non-homogeneous surfaces as did full scale versions, and, not only, without sacrificing versatility and capability, but rather, increasing it. Moreover, none of the prior scatterometers are capable of spherically simultaneously measuring the angular gradiation of the light scattered from a source because none of the light collection systems in any of the prior scatterometers were capable of spherically, simultaneously collecting the reflected light scattered from a spot on a surface of the sample. Applicant's unique collection system has solved this problem.

b. Fiber Optic Bundles

Fiber optic bundles have been known for many years. See, U.S. Pat. Nos. 2,354,591 and 3,033,071 and Siegmund, "Fiber Optic Tapers In Electronic Imaging", Schott Fiber Optics.

A modern fiber optic bundle comprises millions of individual fibers of glass which are first made by pouring pure raw glass of high index of refraction into a tube of lower index of refraction cladding glass, and which are then precisely aligned and fused together to form a solid fiber glass bundle ("boule"). Each fiber sees and carries one small portion of the image by the well known process of internally reflecting light rays emanating from the image. Through this process high resolution images may be efficiently transferred from one surface to another.

During the manufacturing process it is also well known to twist, bend or taper the boule depending on the end function desired. The taper, for example, is made by heating the center and pulling the ends to produce an hour-glass shaped boule with the fibers essentially parallel at the larger diameter ends and smaller diameter center of the boule. During this process the outermost fibers are stretched more and are longer than the innermost fibers. The boule is then cut in half at the small diameter center to provide two identical tapered halves, each of which becomes a fiber optic magnifier/minifier.

Faceplates serve as windows and transmit the image straight through without changing the size or orientation. Twisted bundles function as image inverters. Tapers serve as magnifiers or minifiers. The two end faces of the bundles are preferably parallel planes and may be flat or curved to a desired radius. It is well known to couple the small end of the taper to a self scanned array, such as, a charge coupled device ("CCD") to convert the light level in a group of fibers or "pixels" to a corresponding electrical signal which can be digitized and reconstructed graphically as an intensified image on a computer screen, for example in spectroscope, astronomical and medical applications.

Fiber optic bundles have found wide use in such fields as x-ray image intensifiers and night vision goggles, for example.

As disclosed in U.S. Pat. No. 3,033,071, it is known to further heat segments of the boule and pull the ends of the fibers to form a double tapered, onion shaped boule which is then cut at a point in the tapered portion to form concave surfaces in one or both ends for use as an image or field flattener. In this early device, however, the image is not of a point which is the focal point of the bundle, normal to all fibers and which is a light or a scattered light source that radiates light such that the radiated light strikes the bundle at 0° incidence along the entire surface of the bundle.

As disclosed in U.S. Pat. No. 4,991,971, it is known to have a bundle of equal length optical fibers each end of each of which is arranged in a circular array equidistant from the object being tested and the other ends of which are in a linear array whereby each fiber simultaneously receives a different angular component of the scattered light at the one end and transmits it to the other end such that the transmitted components exit the linear array end simultaneously and are detected and converted to electrical signals by a computer. The constraint of equal length fibers prevents use of a tapered fiber optic bundle in this system. Moreover, the device is limited to reading only that portion of globally scattered light that appears in the single plane in which the circularly spaced fibers are located. Thus, the collection and computation of a scarlet profile for a spherical segment or a full hemisphere requires rotating the sample as in other prior schemes with resultant lengthy, slow construction of the scatter profile.

These deficiencies are overcome in the present invention through the use of a tapered fiber optic bundle, each fiber element of which receives light normal to its aperture from the light source which is at the focal point of the bundle, and which has never before been used in measuring light in a scatterometer. Moreover, a double tapered fiber optic bundle of applicant's unique design provides the remarkable advantages of instantaneous, spherically segmented or hemispherical collection of light from a scatter source and has not been heretofore known.

c. Frame Grabber Algorithms

A frame grabber, or image memory, has been used in the past as part of an image sensor processor. See, U.S. Pat. Nos. 5,040,116, 4,954,962 and 4,843,565. Typically, the frame grabber is contained within a frame grabber pc-board, such as a type made by Coreco or Image Technologies, and is coupled to a data processing device, such as, an 80486 Intel microprocessor driven computer, which, accesses the image memory and, according to a predetermined algorithm, reconstructs the image on a cathode ray tube or other luminescent screen. A standard frame grabber is capable of resolving 256 shades of grey. Where the ambient light has to be eliminated or otherwise adversely influences the reconstruction of the subject image, it has also been known to use a technique of subtracting out the ambient light value from the data. See U.S. Pat. No. 4,991,971 (4:56–64).

Prior frame grabber algorithms have been slow and inefficient and have required the use of expensive CCD cameras. The advantage of applicant's unique algorithm is that its high level of efficiency enables the use of a low cost charge injection device ("CID") camera which eliminates the significant "blooming" problem experienced with CCD cameras when pixels become saturated and which prevents good scatter profile reconstruction.

SUMMARY OF THE INVENTION

Set forth below is a brief summary of the invention in order to achieve the forgoing and other benefits and advantages in accordance with the purposes of the present invention as embodied and broadly described herein.

One aspect of the invention is an apparatus and process for collecting light which comprises a plurality of optical fibers the one ends of each of which are fixed in spaced relation to each other, in a curved surface having substantially a radius of curvature normal to each fiber and the other end of each of which is arranged in an indexed array, and the longitudinal axis of each fiber at the one end substantially converges at the common point, whereby light radiating angularly from the point is received simultaneously at the one end by each fiber and is transmitted to the other end.

Further features of this aspect of the invention include embodiments wherein the curved surface is a full hemisphere, a spherical segment or a linear segment.

A second aspect of the invention is an apparatus and process for measuring light reflected from a surface including a housing, a laser diode light source for illuminating the surface and supported within the housing, a tapered fiber optic bundle supported within the housing and having a concave face on the tapered portion at one end, with the other end formed as a flat array adapted for transmitting light reflected from a point on the surface, and a CID camera supported within the housing and having a scannable area array for receiving the transmitted light beams and converting the beams to electrical signals.

A further feature of this aspect of the invention is controlling the power of the laser by controlling its on time.

A third aspect of the invention is an apparatus and process of acquiring with an x-y scannable array camera light reflected by a subject that may exceed the dynamic range of the camera including the steps of a) measuring the ambient light and storing the measurement in a reference frame, b) illuminating the subject with a laser diode light source for a predetermined time period, c) collecting the light beams reflected from the subject during the on period and transmitting the beams to the array, d) digitizing the collected data by x-y scanning the array and converting the light beam to electrical data, e) storing the digitized data in the next frame, and f) repeating steps (b) to (e) while increasing the on time of the laser diode by predetermined amounts (for example, one order of magnitude) during each repetition, whereby a reference frame and N data frames are collected and stored in N+1 sequential frames.

A fourth aspect of the invention is an apparatus and process of reconstructing a single data profile from the data stored in the plurality of sequential x-y oriented memory frames of the computer frame grabber the first frame of which is a reference frame in which the data represents a factor common to all frames in the sequence, and the remaining frames of which are data frames including the steps of a) setting an x-y oriented profile array in memory and filling the array with zeros, b) computing a scale factor, c) subtracting the common factor data (i.e. ambient light) in the reference frame from the data in each of the data frames in the sequence, d) scaling the data in the first data frame by the scale factor and adding the scaled data to the profile array, e) scaling and adding the data stored in each x-y point in the next succeeding data frame to its corresponding x-y location in the profile array only if data has not been previously stored in that location, and if (1) the data already in that x-y point in the array is zero, and (2) the data in that x-y point in the current and any prior data frame is less than T, where T is a threshold level representing a level above which the data is invalid, and f) repeating step (e) separately in sequence for each subsequent data frame in the sequence.

A fifth aspect of the invention is a scatterometer apparatus and process for measuring light reflected angularly from a point which includes a power controlled laser light source for illuminating the point, a fiber optic bundle focused on the point for collecting light beams reflected therefrom, a camera for converting the reflected light beams into electrical signals, the signal level of the collected light beams being raised above the dark current noise level of the camera by sequential increases in the on time of the laser by predetermined amounts to form sequential images stored in a frame grabber, and the frame grabber also sequentially digitizing the stored images and reconstructing therefrom a single scatter profile of the point while simultaneously scaling out the order of magnitude increases.

A further feature of this aspect of the invention is that the scatter profile may be completely reconstructed within one second.

A sixth aspect of the invention is the process of collecting light in a scatterometer to convert the light to electrical signals which includes the step of directing the light into a tapered fiber optic bundle. A further feature of this aspect of the invention is directing the optical fibers in the bundle such that they have a common field of view.

A seventh aspect of the invention is the method of manufacturing which includes forming a tapered fused fiber optic bundle and cutting a concave face in the tapered portion normal to the bundle such that all of the fibers have a common field of view.

The principal advantages of the scatterometer of the present invention are its compact size, ruggedness, speed, and hemispherical capability.

This new, table top, portable instrument is the fastest, most powerful scatterometer on the market. It allows high resolution (0.125°) which can be increased by using higher density CID arrays, partial or full measurement of hemispherical scatter data in less than a second with no moving parts from a very small 12"×10"×6" footprint.

This new technology enables taking hemispherical, rather than curvilinear, data measurements with negligible change in cost, while providing greatly increased performance benefits.

The fiber optic bundle scatterometer ("OMNISCATR"™) of the present invention has the ability to measure light scatter caused by everything from scratches, blemishes, bubbles, subsurface defects, and surface roughness ("RMS") to BRDF AND BTDF. It measures over 200,000 points over the hemisphere, two orders of magnitude more spatial data than any known scatterometer, thus, enabling detection of defects regardless of orientation, and determination of the orientation itself.

Until now, scatterometers have been mainly used in the aerospace industry. The new generation scatterometer of the present invention, however, with its higher speed, smaller size and lower cost is available as a quality control device to many other industries that require assurance of high surface quality, such as, for computer screens, precision bearings, flat and power optics and specially coated or painted surfaces.

BRIEF DESCRIPTION OF THE DRAWINGS

FIG. 7B is a possible front elevational view of FIG. 7.

FIG. 10 is a side elevational view of an alternative embodiment of the front half of the tapered bundle of FIG. 8 with a higher angled taper than FIG. 11A.

FIG. 11A is a side elevational view of an alternative embodiment of the front half of the tapered bundle of FIG. 8.

FIG. 11B is front elevational view of FIG. 11A.

DETAILED DESCRIPTION OF THE PREFERRED EMBODIMENT

TABLE OF CONTENTS

I. DEFINITIONS

II. INTRODUCTION

III. INSTRUMENT DESCRIPTION

Figure 1:
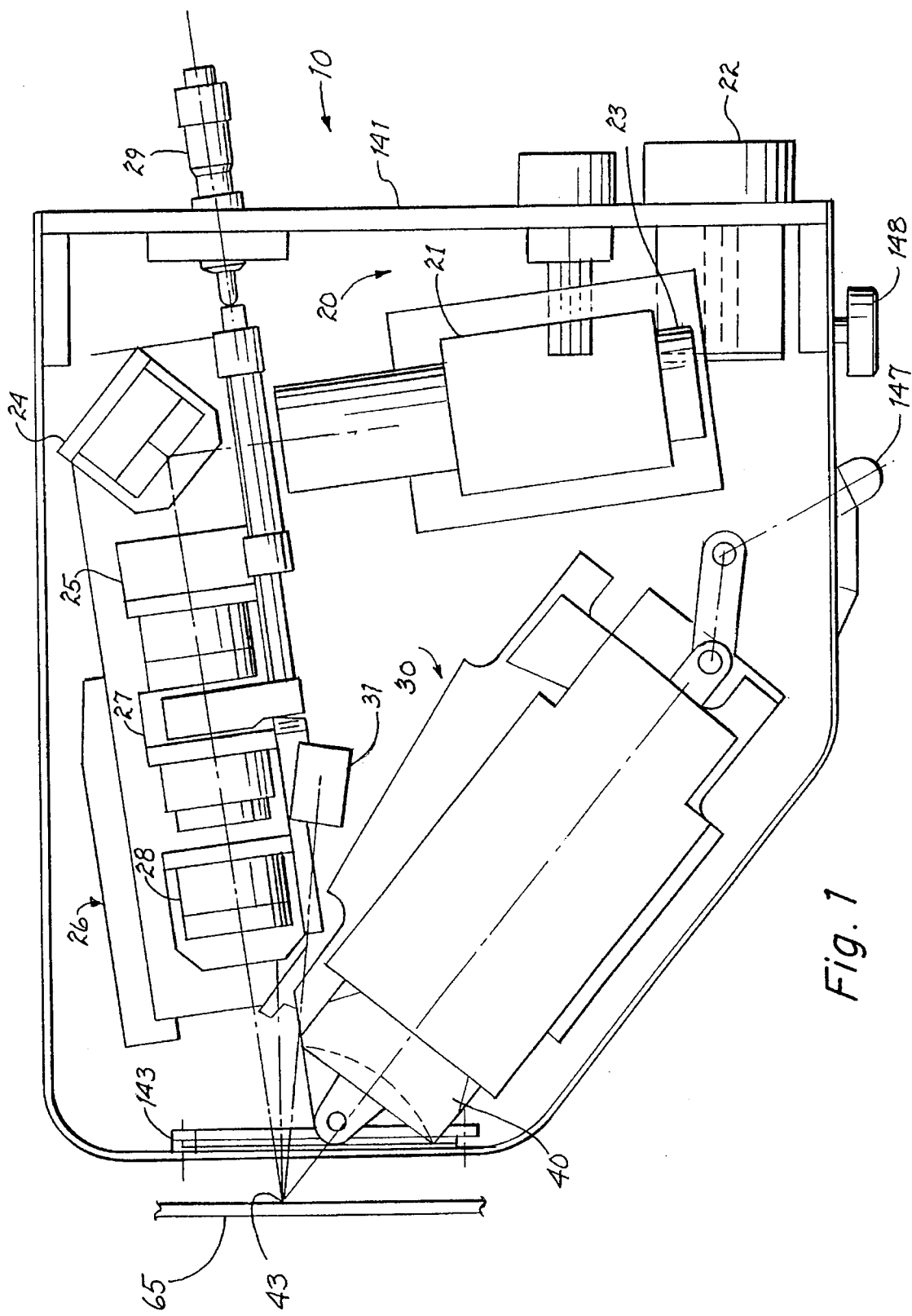
FIG. 1 is a top plan view in partial section of the interior of the housing showing the measurement head containing the laser source, collection optics, beam dump and camera assembly.

A. Overview
B. Optical Layout
1. Source Section
   a. Laser Diode
   b. Cornu Psuedo—De Polarizer
   c. Focusing Optics
2. Collection System
   a. Tapered Fiber Fundle
      (1) Unitary Double Tapered Fiber Optic Bundle
      (2) Full Hemisphere Fiber Optic Bundle
      (3) Fused Unitary Double Tapered Fiber Optic Bundle
      (4) Partial Tapered Fiber Optic Bundle
      (5) Linear Array Fiber Optic Bundle
   b. Fiber Optic/Camera Assembly
   c. Optical Filter
3. CID Camera
4. Enclosure & Adjustments
   a. Housing and Mounting Plate
   b. Compactness Of Measurement Head
   c. Protective Shutter
   d. Ruggedness Of Measurement Head

IV. ALIGNMENT

A. Internal Alignment
B. External Alignment

V. DATA ACQUISITION HARDWARE AND SOFTWARE

A. Computer Hardware Interface
B. Software User Interface

C. Data Acquisition and Data Reconstruction
1. Ambient Light Compensation
2. Scatter Measurement/Data Acquisition
3. Data Reconstruction
D. Data Display
E. Data Analysis
1. Normalization
2. Calibration
3. System Profile
4. Volume of Information
F. Data Storage
G. Two Dimensional Plotting
H. Three Dimensional Plotting
I. Graphic Output

VI. ADDITIONAL MEASUREMENT TECHNIQUES

A. Rapid Surface Scan
B. Processing and Surface Analysis

VII. TECHNICAL NOTES AND CALCULATIONS

TECHNICAL NOTES
Detector Linearity
Calibration
RSS Calibration Method
ABDM Calibration Method
Stray Light Control
CALCULATIONS

| DEFINITIONS | |
|---|---|
| TERM | MEANING |
| BRDF | Bidirectional Reflective Distribution Function |
| BTDF | Bidirectional Transmission distribution Function |
| BSDF | Bidirectional Scatter Distribution Function |
| TIS | Total Integrated Scatter |
| RSS | Reference Sample Substitution method |
| RMS | Surface Roughness |
| PSD | Power Spectral Density |
| ABDM | Attenuated Input Beam Direct Measurement |
| HgCdTe | Mercury Cadmium Telluride |
| NIST | National Institute of Standards & Technology |
| FASCAT | Fully Automated Scatterometer |
| Sample Detector | Detector which intercepts scatter from the sample |
| Reference Detector | Detector which monitors laser fluctuations and attenuation |
| SNR | Signal-to-Noise Ratio |
| LVND | Linear Variable Neutral Density |
| AR | Anti-Reflective |
| CCD | Charge Coupled Device |
| CID | Charge Injection Device |
| TTL | Transistor To Transistor Logic |
| Source Head | The laser radiation source with beam shaping and collimation in an enclosed compact unit. |
| Collection Head | All collection optics and the detector on a small base plate. |
| Measurement head | An enclosed unit to be mounted on a production machine containing the source head, collection head, external focus control, shutter, and mounting accommodations. |

II. INTRODUCTION

The detailed description of the invention has been divided into several major sections. The first section, Instrument Description, contains a brief overview and describes the functional components of the scatterometer. The next section describes the internal and external alignment of the measurement head. The data acquisition and software section describe the control of the scatterometer, the analysis of the data and, by its nature, the use of the instrument.

III. INSTRUMENT DESCRIPTION

A. Overview

Figure 2:
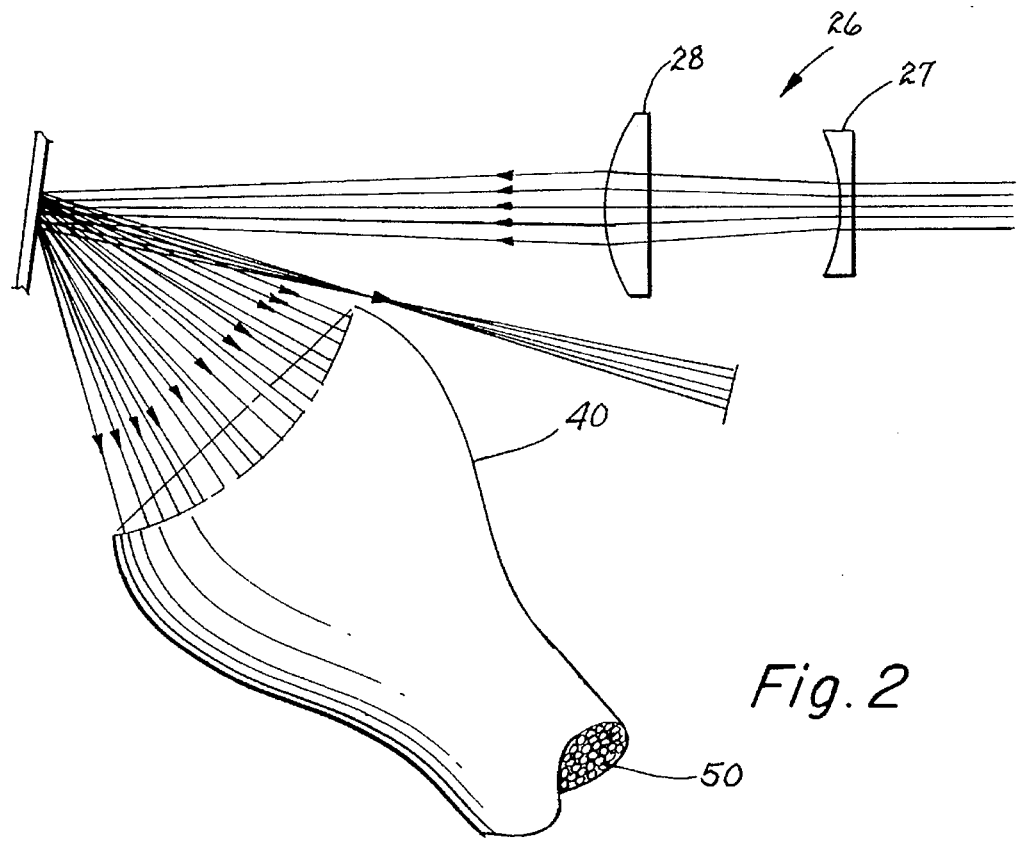
FIG. 2 is an optical schematic drawing showing focusing of the laser source light rays on the beam dump and optical collector.
Figure 16:
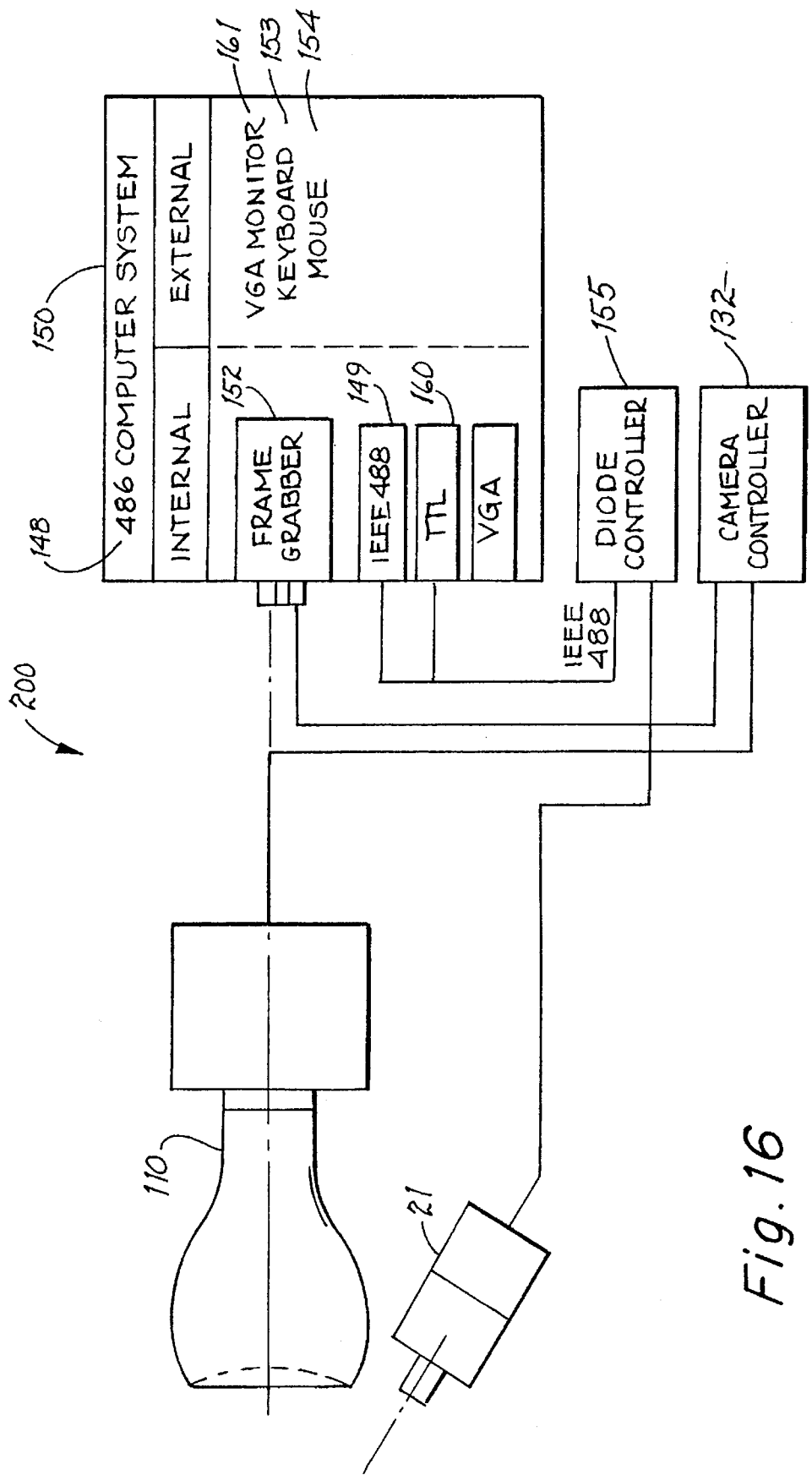
FIG. 16 is a schematic block diagram of the scatterometer data acquisition system which includes a computer, frame grabber, IEEE-488 card, TTL card, and a laser diode controller.

An overview of the measurement unit 10 and the data acquisition and reconstruction 200 system of the new scatterometer design are shown in FIG. 1 and 16, respectively. The scatterometer of the present invention incorporates two uniquely distinctive concepts. The first is the incorporation of a tapered fiber optic bundle 40 (FIGS. 2 and 4) to collect the scattered light from the sample 65. The second is a data acquisition algorithm 170, 180 (FIGS. 17, 18) that allows rapid collection of the five orders of magnitude of light required without using the traditional slow detector/lock-in amplifier pair technique used in current scatterometers. Some advantages offered by this design include:

Hemispherical data acquisition in less than 1 second

Resolutions of up to 0.125° or higher

Measurement of in-plane and out-of-plane scatter

Using a collection of many fibers 44 (FIGS. 2, 4) fused together with a concave face 41 cut into the tapered section 48 of the bundle, scatter data can be collected and directed to a camera 130 for very fast data collection. This aspect of the invention allows all of the data to be collected simultaneously, eliminating many undesired repetitious measurements based on time related variables. To get the low signal levels required for at least $10^{-5}$ BRDF, the laser power and/or camera integration time will be controlled to raise the signal level above the dark current noise in the camera. A method 170 has been developed to control the laser power so that the data can be collected approximately one order of magnitude at a time. With a conventional frame grabber digitizing multiple camera images, each order of magnitude of data can be collected separately and used 180 to reconstruct the scatter profile. At 30 frames/second collection rates, the time to collect the data is well under a second.

The detailed description of the instrument section of the scatterometer is further divided into several sections to facilitate a complete system description. These sections are optical layout and specification summary, source optics 20, collection optics 30, CID camera 130, and the system enclosure and adjustments 140.

Working examples of the scatterometer are set forth in Table 1 which sets forth a component summary of the measurement head characteristics, Table 2 which shows the instrument's overall parameters, and Table 3 which describes the instruments data acquisition and software characteristics. More technical notes such as stray light control and CID camera calculations are included in Section VII below.

B. Optical Layout

Figure 7:
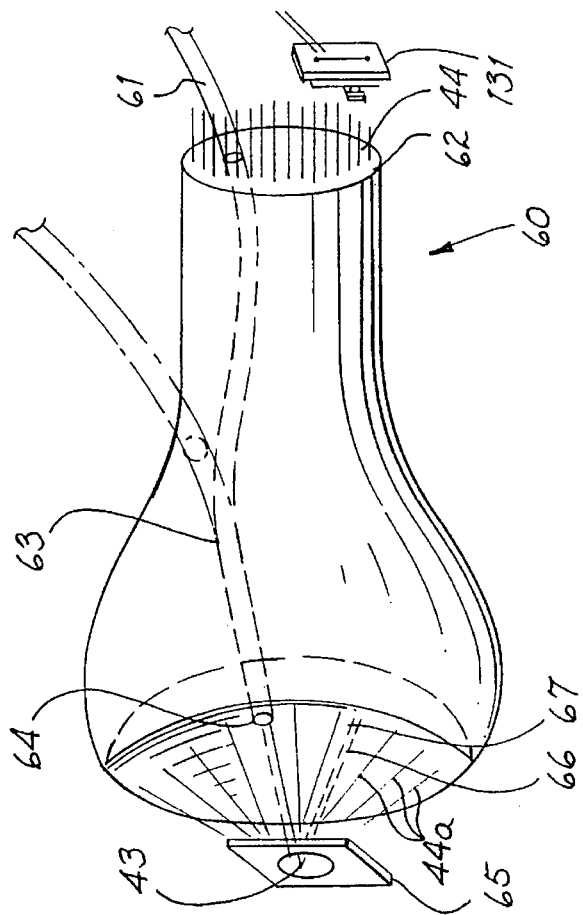
FIG. 7 is a perspective view of yet another alternative embodiment of the single, hemispherically cut, tapered fiber optic bundle of the present invention with the light source going through the bundle.

The optical layout is shown in FIGS. 1, 2, 3, 4 and 13. As best seen in FIG. 1, the optical layout includes the laser diode 21 and controller 22, fold mirror 24, psuedo-depolarizer 25, focusing optics 26, shutter assembly 143, beam dump 31, and fiber optic/camera and camera controller assembly 30 with camera imaging array 131 (FIG. 7).

1. Source Section a. Laser Diode

To obtain ample power in a small package a conventional laser diode 21 is used as the laser source. The laser diode 21 is powered and controlled within the housing 141 by the laser connector 22. The laser beam is directed to and reflected by a fold mirror 24 supported in the housing 141 at an angle.

The particular diode and power chosen is based on the minimum BRDF of $10^{-5}$ $sr^{-1}$, optimal reception characteristics of the collection optics, and the camera sensitivity. There is a trade off in selecting laser diode power and wavelength. Visible camera sensitivity is at a peak around 670 nm, while diode power peaks around 840 nm or higher. As shown in the power calculations, the laser power and wavelength are optimal at 70 mW and 840 nm respectively. The diode unit 21 is complete with beam circularization (beam forming) and a collimated output beam of 7.5 mm. The diode unit 21 includes a driver (not shown) for power stabilization, thermoelectric cooling, and TTL/Analog modulation. The cooling is required since power output, which must be held constant, is temperature dependent. TTL modulation 160 is used to pulse the laser diode 21 or turn it on for a specified time, thus controlling the amount of power on the sample 65 and detector array 131. The lifetime of the laser diode 21 is about 50,000 hours.

In the preferred embodiment the laser diode controller controls the amount of power on the camera to five orders of magnitude. Laser diodes are typically only adjustable in power level over one to one and one half order of magnitude. So the alternative is to control the time that the power is incident on the camera. The controller 23 is set to modulate the time the laser is on from a range of 10 ns to continuously on. This capability yields several orders of magnitude of BRDF range above what is required. The rise-fall time of the laser power output is also in the 10 ns range. This range is sufficient to allow control of the incident laser energy over more than the required five orders of magnitude. The laser timing is controlled through the use of a TTL 160 level initiate signal provided by the computer system 150 and loading the controller 23 with the desired power level through an IEEE-488 interface 159.

The output power per pulse is controllable to a maximum specified for the laser. The controller 23 has the ability, through the use of a photodiode feedback loop (not shown), to both stabilize and measure the power output.

Power and timing calculations are provided in Appendix B.

A working example of a laser diode unit 21 is a Model 06 PLL 807 made by Melles Griote and has the following characteristics:

833 nm beam wavelength (required visible to 3.0 microns)

70 mw power output of the laser unit 7.5 mm collimated circular beam (internal beam shaping)
  beam profile is $R/e^2=3.4$ mm
  3 part collimating lens—spherical aberration correction and collimation
  cylindrical lens—astigmatism correction
  anamorphic prisms—circular beam shaping Thermoelectrically cooled External power supply/controller Melles Griote MOdel 103 allows full control of laser power, temperaturel and on/off time Pulse modulation up to 1.0 MHz (used to control power output)

b. Cornu Pseudo-depolarizer

Due to the use of a laser diode 21 in the measurement head 10, the source section 20 starts with linearly polarized light. Since no true depolarizers exist, the laser light is spatially randomly "depolarized" through the use of a cornu pseudo-depolarizer 25. Careful attention to the beam size and intensity pattern is required to achieve a high degree of depolarization. Depolarization efficiencies of better than 95% are attained which is sufficient to achieve the desired accuracy of BRDF.

It is sometimes useful to use polarized light, but in general BRDF measurements should be taken with unpolarized light, randomly circular polarized light, or, if need be, circular polarized light. Relating mathematically the s or p polarization sources to the scatter and the surface characteristics, and then compensating for the polarization effects in software is a complex problem. To avoid this problem a pseudo-depolarized laser beam is used for the measurements. activity in crystalline quartz. It operates on collimated beams of light, transforming linear polarization states into a complicated and spatially changing continuum of linear polarization states.

c. Focusing Optics

As shown in FIG. 1, the output of the laser/depolarizer assembly is directed onto the sample and focused on the collection optics with focusing lenses which function as an inverted telephoto system, i.e. a negative and positive lens system.

The lens system 26 is designed to minimize the collection aberrations from the negative lens 27 and positive lens 28, each of which has a nonreflective coating.

The lenses are a good quality achromat and are adjustable to control the focus of the beam with respect to the fiber optic bundle 40. The adjustment of the focus lenses 27, 28 allows for proper compensation for powered optical surfaces. However, the range of the adjustment may be restricted by the small size of the measurement head.

Focus adjustment is performed manually by a micrometer 29. Approximately 3 mm of micrometer travel is required for infinite (flat surface) to 600 mm (concave surface) radius of curvature. The focusing optics 26 produce approximately a 4 mm Gaussian spot size on the sample. Diffracted energy from the test sample not striking the fiber bundle is kept well within 2°.

2. Collection System

As best shown in FIGS. 1, 3, 4 & 11 the collection optics 30 include a tapered fiber optic bundle and a camera. The tapered fiber bundle which collects the scattered light is directly connected to a solid state, CID camera.

a. Tapered Fiber Bundle

There are several embodiments for the fiber optic bundle of the present invention.

(1) Unitary Double Tapered Fiber Optic Bundle

Figure 4:
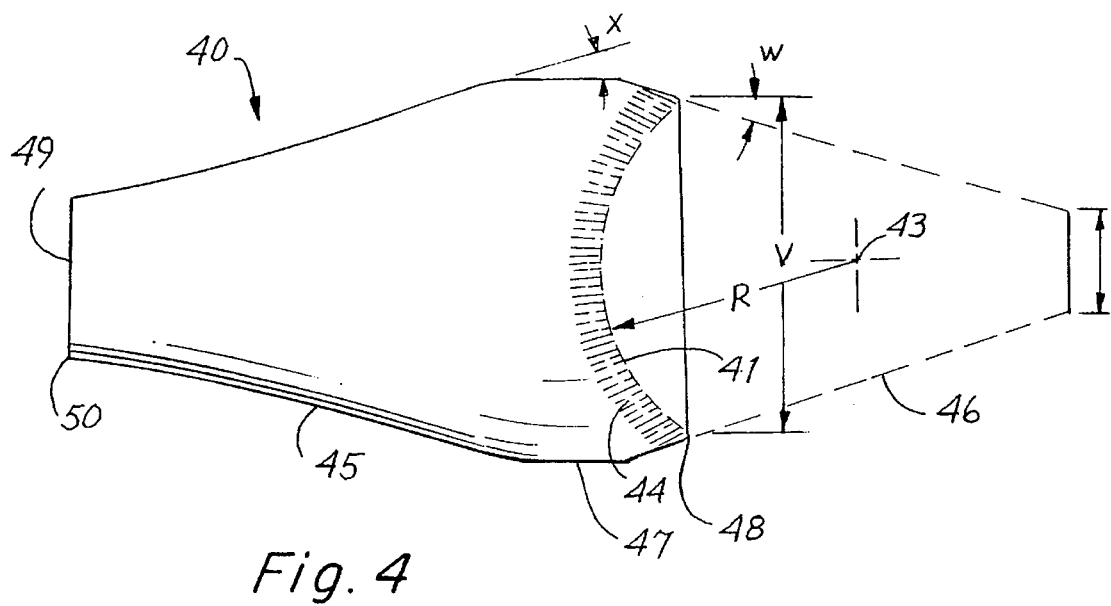
FIG. 4 is a plan view in partial section of the onion-shaped boule from which the preferred embodiment of the double tapered fused fiber optic bundle of the present invention is made, and, further shows the radius of curvature cut into the converging tapered area to form the concave front face of the bundle.

As seen in FIG. 4, the preferred embodiment is a one piece double tapered fiber optic bundle 40 with a concave face 41 cut into the tapered portion 48 at one end. Prior to the spherical cut forming the front face, the boule is shaped like an onion. The fiber bundle is a single piece of glass made of fused 25 um diameter fibers 44 tapered down to 3.8 um diameter by a well known process of heating, stretching and cutting. The bundle 40 provides approximately 40% transmittance. The radius of curvature R on the front face 41 is required so that all fibers 44 have a common point of view and are, thus, viewing the same point 43 on the sample. This construction provides the enhanced functionality of partial or full hemispherical measurements depending on the type of fiber optic bundle used and the way in which the source light is applied.

Figure 5:
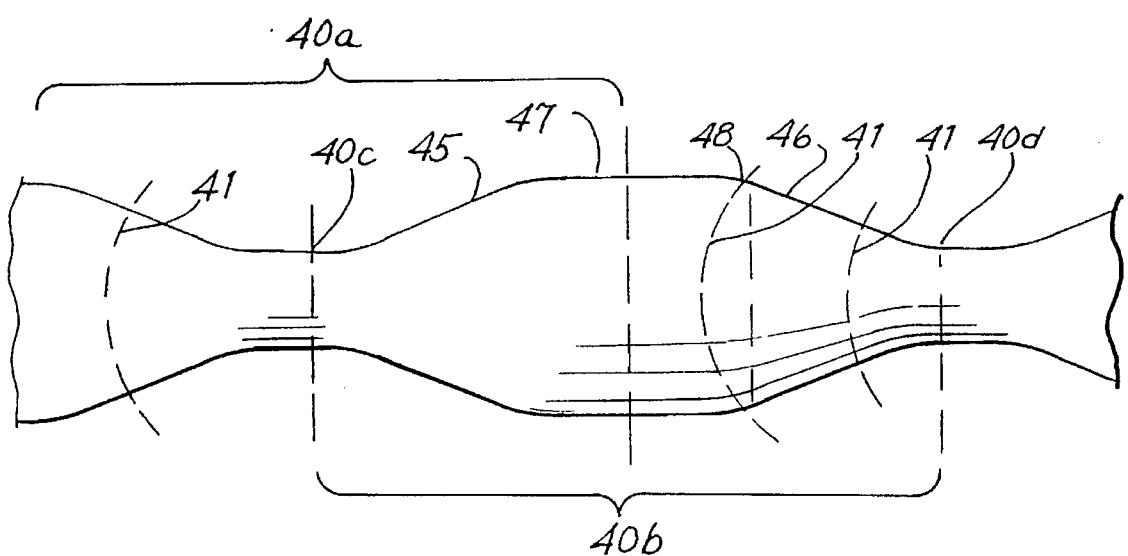
FIG. 5 is a side elevational view of a double tapered fiber optic bundle of the present invention prior to its being cut into individual bundles.

In the preferred form of the invention, a unitary double tapered fiber optic bundle 40, the bundle is stretched a first time to produce the well known hour-glass shape having a narrow portion in its center with wide portions at its ends as seen at 40a in FIG. 5. Then, each of the wide ends is stretched a second time to produce the new onion shape having a narrow section at each end and a wide section in the middle as seen at 40b in FIG. 5. Now, when the bundle is cut at the narrow sections 40c, 40d, what is left is a boule 40 which looks like an onion as shown in FIG. 4 in that the wide portion 47 of the taper is in the center and the narrow portions 45, 46 of the taper are at each end. The spherical cut 41 is then placed at a point in the tapered portion 43 near the wide center 47 where the fibers 44 are converging to form the unitary double tapered shape 40 shown in FIG. 4. As further seen in dotted lines in FIG. 5, spherical cuts 41 may be placed at other desired locations on the taper where the fibers are converging or diverging. The end 49 is cut in a flat planar surface forming an indexed array adapted to be mated to a camera for converting the transmitted light to electrical signals.

As shown in FIGS. 4, 10, 11A and 13, the desired curvature is obtained automatically from the tapered fiber optic bundle by cutting the face 41 at a selected radius R at the converging point 48 of the taper to form a spherical surface in the tapered bundle where the individual fibers are converging. The cut is made roughly perpendicular to each fiber 44 in the bundle 40 regardless of its position. The preferred radius on a 2" diameter boule gives a 40° to 60° three-dimensional cone angle measurement range of the light scatter from the spot on the sample which is the focal point of the concave surface 41. All individual fibers 44 within the bundle have a common light source 43 field of view. The longitudinal axis 43a (FIG. 6) of each fiber 44 is normal to the cut of the bundle 40. In addition each incident ray 44a (FIG. 7A) of light emanating from the focal point of the bundle and striking a fiber is normal to the cut of the bundle at the point it enters the fiber. While each fiber's surface normal may actually hit the sample surface at various locations within the illuminated spot, nevertheless, the effect of this slight deviation is averaged out, since each fiber 44 collects the scatter of the entire illuminated area only at its viewing angle.

A working example for FIG. 11A is as follows:

Outside diameter of bundle=2"

Inside diameter at cut point 48=1.75"

R=2.12"

d=47°

A narrow (830 nm) waveband anti-reflective filter coating can be put on the back face 49 or front face 41 of the fiber bundle 40 which is very durable. This reduces unwanted light of other wavelengths.

Some advantages of the fiber bundle 40 are that a high density of camera detector elements may be mated to the small end of the taper (minifier function) and three dimensional out-of-plane measurements may be taken at high speed.

Stray light reflections from the faces of the fiber bundle 40 itself are controlled by the use of a good quality AR coatings. The specular reflection off of the polished AR coated face of the fiber bundle would create a scatter signal that would exceed the expected measured signal by orders of magnitude at the far angles. Even a black spot painted on the fiber bundle at the specular position would create appreciable stray light. For a specular measurement the light trap needs to be a sophisticated combination of a specular black surface and a diffuse absorber. For this reason the specular beam is excluded and a beam dump 31 for the specular beam has been included.

Currently the collection optics can be swung into the specular position and out again for separate specular and low scatter measurements. Future versions of the fiber shell may allow simultaneous measurement of near specular and far angles (low scatter) if a good solution is found for suppressing the specular beam.

The collection system 30 is susceptible to ambient light. Ambient light is controlled through the use of a narrow band filter. It is recommended that fluorescent lights be used in the measurement room, since they have lower emission in the 0.670 μm to 0.900 μm region, which is an operating wavelength region of the scatterometer. Any remaining ambient light up to a certain threshold can be subtracted out of the data after it is acquired as discussed below in the data acquisition section.

Analysis results have shown a worst case stray light condition of one order of magnitude above the desired scatter level when the specular beam is incident on the fiber bundle. When the specular reflection is directed into the beam dump no stray light problems have been encountered.

(2) Full Hemisphere Fiber Optic Bundle

Figure 6:
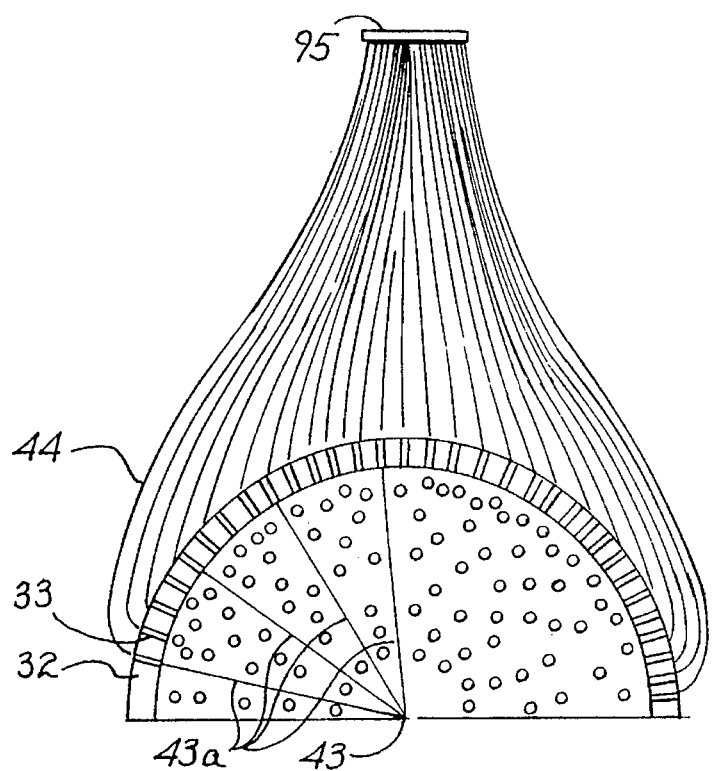
FIG. 6 is side elevational view in cross section of a fiber optic bundle of the present invention using single fibers in the form of a full hemisphere.

Shown in FIG. 6 is yet another embodiment of the fiber optic bundle of the present invention. In this form of the invention a hemispherical dome 32 which is one half of a full sphere is made of any rigid material and is pre-drilled with a plurality of radial holes 33 the common field of view of which is the center of the sphere 43. A fiber optic 44 is inserted and secured within each radial hole 33. The fibers are then bundled together and the loose ends are arranged into an array 95 such as is shown in FIG. 12D. Any one of fibers 44 may function as a conduit for the laser diode 21 source light to illuminate the point 43 on sample 65. Alternatively, a fiber 44 may be removed and replaced by a conduit for the light from laser diode 21. If stray light is not a problem, the specular beam is used for measurements. If stray light is a problem, a hole may be drilled in dome 32 allowing the specular beam to pass through the dome thereby essentially eliminating the stray light. This form of the invention is used by placing the hemi-dome 32 over the point on the surface to be measured and illuminating the surface with the laser diode source 21. Full simultaneous hemispherical measurements of light scattered by the point sample are enabled because all fibers in a full hemisphere have a common field of view at that point.

(3) Modified Fused Unitary Double Tapered Fiber Optic Bundle

A further embodiment of the double tapered fiber optic bundle 60 is shown in FIG. 7A. In this version of the bundle, the laser source beams are directed onto the sample through an enlarged fiber 61 or through a longitudinal hole in the fiber which begins at the small end 62 or through a side wall 63 of the bundle and terminates on the spherical face 64 cut into the converging portion of the large end of the bundle 60. In this form of the invention, the laser source beam is transmitted to the sample 65 through the fiber bundle 60 and the specular beam 66 is reflected to a black spot 67 painted on the spherical face. Partial hemispherical measurements may be simultaneously made of the scattered light from the light source 43 which are then carried and reflected through the fibers 44 to the small end 62 of the taper 60 which terminates in an indexed array as shown in FIG. 7A and is adapted to be mated to a CID array camera 130. The light reaching the small end of the taper is converted to electrical signals through the CID array 131 in the camera 130 and then is digitized in the frame grabber 152 and displayed by the computer 150.

Figure 8:
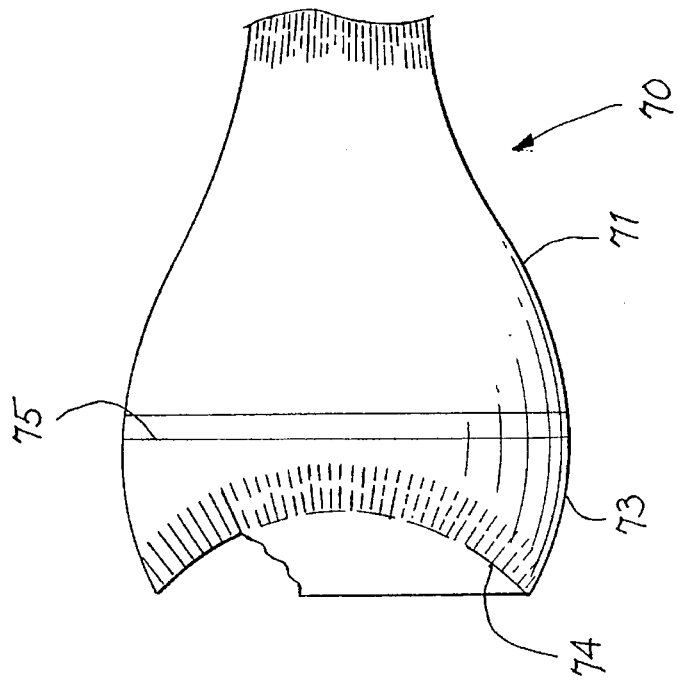
FIG. 8 is a perspective view of yet another alternative embodiment of the single, hemispherically cut, tapered fused fiber optic bundle of the present invention made in by cutting and fusing together two separate halves.

Still another embodiment for the fiber optic bundle 70 of the present invention is shown in FIG. 8. In this embodiment the fiber optic bundle 70 comprises two-halves 71, 73. One-half 71 is a standard fiber optic bundle with flat faces at both ends. The other half is also a standard fiber optic bundle which has a hemispherical cut 74 in its front face in the converging portion of the taper. The other face (wide end) 75 is flat. The two flat faces 75 at the wide ends of the tapers are rotated 45° relative to each other and are then bonded together using conventional bonding material to form a unitary double fiber optic taper. The purpose of the rotation is to eliminate any moire effect.

(4) Partial Tapered Fiber Optic Bundle

Figure 9:
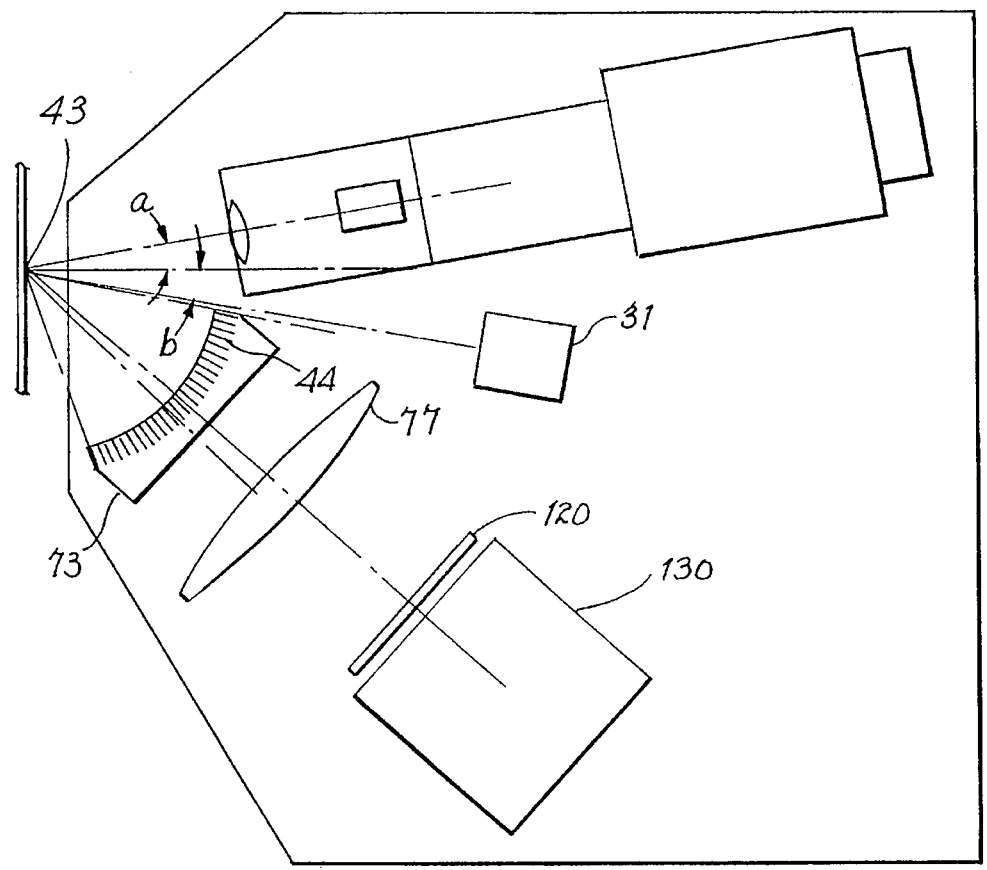
FIG. 9 is a schematic top plan view of an alternative embodiment of the interior of the housing showing the source, collection optics, and camera. Only a partial tapered fiber optic bundle is used the end of which is imaged onto the detection array.

Shown in FIG. 9 is an alternate embodiment of the collection system 30. In this approach only a portion 73 (one half as shown in FIGS. 10 and 11A) of the tapered fiber optic bundle is used, and an imaging system is used to focus the light onto the camera detector array 131.

In this embodiment the AR coated focusing lens 77 has a diameter larger than the outside diameter of fiber bundle 73 to collect all of the light emitted from the opposite end of the fiber bundle and focus it on the camera detector array 131 in camera 130. Since there are many more fibers 44 than there are pixels it is possible to move the camera in and out to focus on portions of the image, thus achieving even higher resolution measurements, possibly up to 0.05°.

(5) Linear Array Fiber Optic Bundle

Figure 12A:
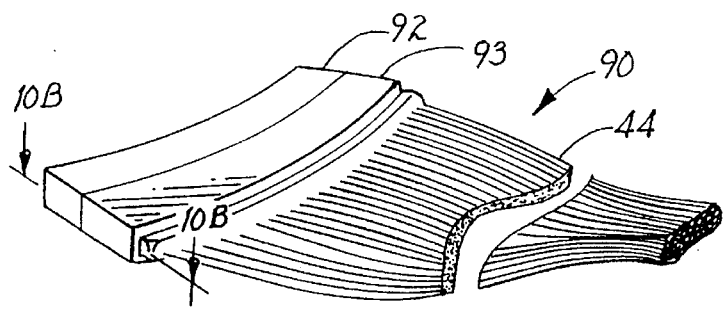
FIG. 12A is a perspective view of yet another alternative embodiment of a linear type fiber optic bundle of the present invention (fused or single fibers).
Figure 12C:
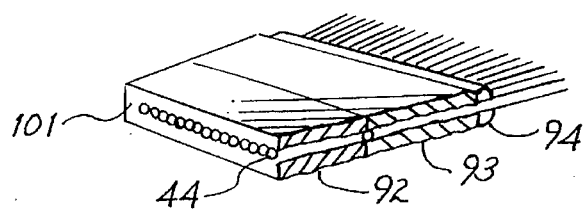
FIG. 12C is a further perspective view of the bundle shown in FIG. 12A.
Figure 12B:
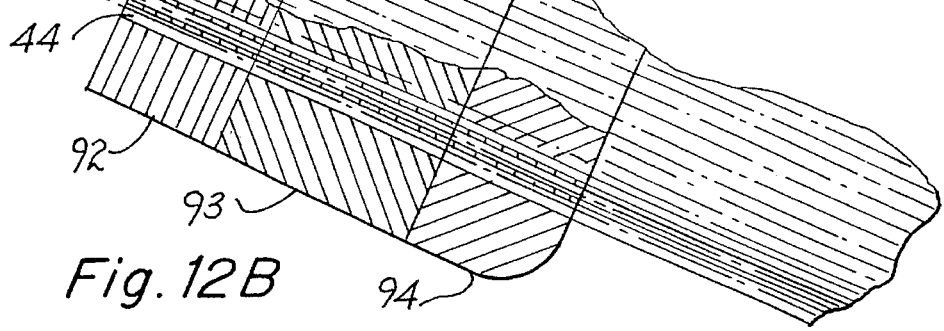
FIG. 12B is a plan view in partial section of the bundle shown in FIG. 12A.
Figure 12D:
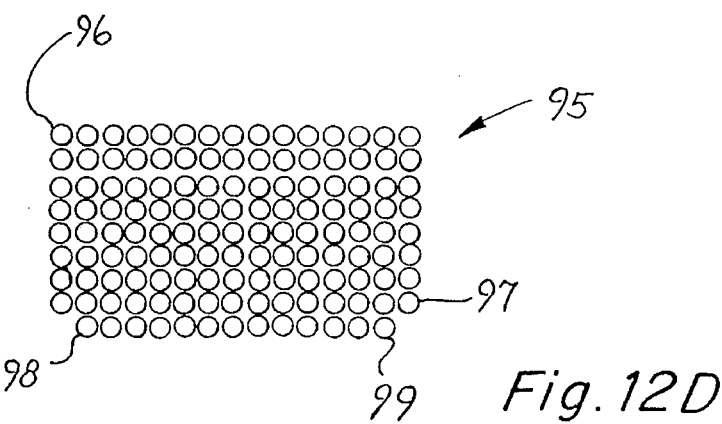
FIG. 12D is a rear elevational view of small exit end of the bundle shown in FIG. 12A formed into a matrix for attachment to the CID camera array.

Shown in FIGS. 12A, B, C, D and E are several views of yet another embodiment of the fiber optic bundle of the present invention. In these figures is shown a linear array type fiber optic bundle 90. As shown in FIG. 12A, a working example includes 133 400 micron diameter fibers 44 orientated in the aperture blocks 92, 93 which have been preformed for the fibers 44 to be inserted at 0.25° spacings such that the 133 total fibers 44 cover 33° field of view directed at a single point 43 (not shown) on the sample. The assembly is then bonded by potting 94 compound which adheres the fibers to the aperture blocks as shown in FIGS. 12B and 12C.

Figure 12E:
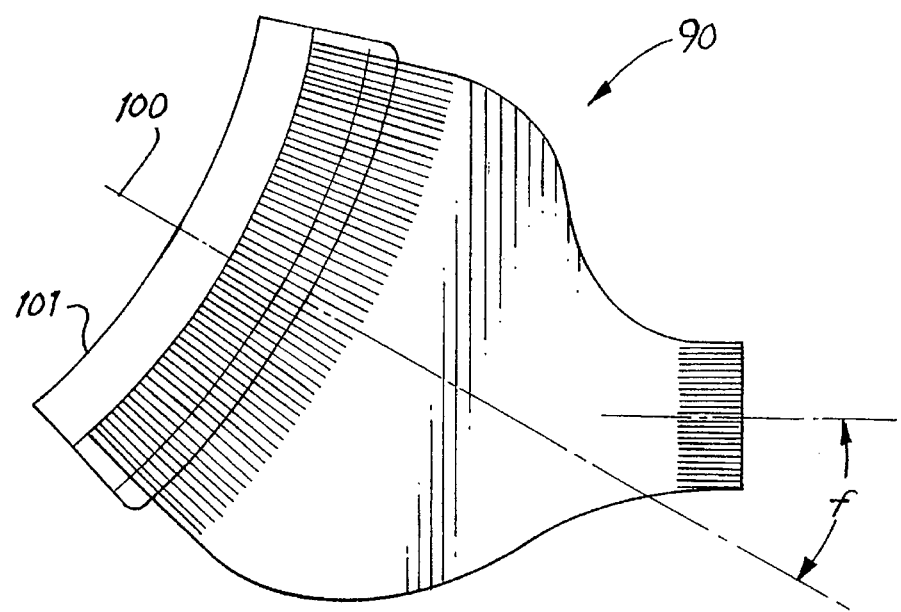
FIG. 12E is a plan view of the bundle shown in FIG. 12A.

The other end of the fibers 44 are brought together in an array 95 of smaller but thicker dimension as shown in FIG. 12D which can be readily mated to the CID camera. A working example of the small end array 95 is approximately 6 millimeters wide and 4 millimeters high and comprises 8 rows of 15 fibers, numbers 1 96 to 120 97, with the bottom row containing 13 fibers, numbers 121 98 through 133 99. As a further working example shown in the plan view FIG. 12E, the central axis 100 of the linear array 90 of the fibers at its wide end is orientated f=28 to 29 degrees from the central axis of the small end of the fibers. The front face 101 of the linear array 90 is flat and perpendicular to the central axis of its plane of curvature.

b. Fiber Optic/Camera Assembly

Figure 13:
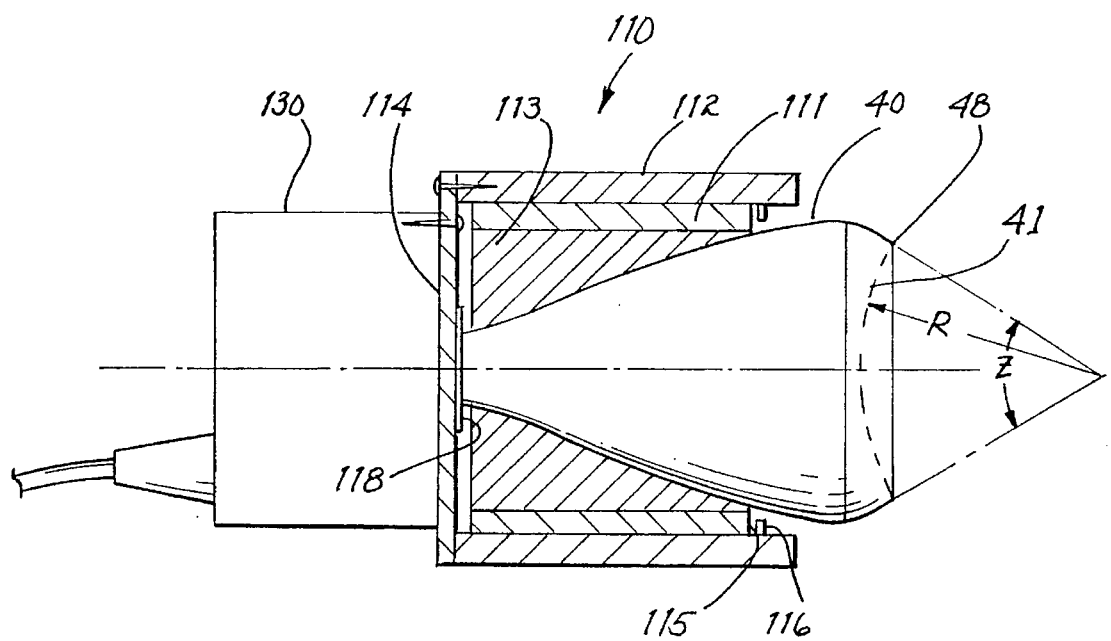
FIG. 13 is a side elvational view of the fiber optic assembly unit showing its mounting in its encapsulation fixture and spring based attachment to the CID camera.

Finally, as shown in FIG. 13, the double tapered fiber optic bundle 40 of the present invention is seen in its encapsulated form in its housing attached to the camera head unit 130 which forms the fiber optic camera assembly 110. The mated CID camera and fiber optic bundle assembly 110 allow 90% transmittance. A fiber optic face plate 118 replaces the standard glass window used in most arrays. The small tapered end of the bundle 40 is spring loaded 115 against the fiber optic face plate 118 in the camera head unit. The camera head unit 130 is fixed to the housing 112 which receives the fiber optic taper 40 and is mounted thereto by a mounting plate 114. The fiber optic taper is located within the encapsulation fixture 111 within the housing 112 with potting 113 filling the vacant areas and providing a seat for the fiber optic taper. A spring 115 holds the encapsulation fixture firmly against the fiber optic face plate by having its other end abutting the spring retainer 116.

c. Optical Filter

An optical filter 120 (FIG. 9) is selected to match the source wavelength which can be coated on the front or back surface of a taper or be a separate filter in front of the camera or collection optics. This eliminates a large portion of any stray ambient light.

3. CID Camera

The measurement requirements place unusually high demands on the detection electronics. A single element detector is not feasible due to the required resolution and measurement time. The mechanical requirements for scanning the device are also prohibitive. Linear array detectors are readily available, but when compared to area array detectors they are just as expensive and require less convenient support electronics. An area array camera is selected for data acquisition as the best cost performance alternative since it is sold in a more competitive market, is available in a wide variety of formats, and provides larger data capacity.

An area array CCD camera based on raw BRDF data requirements is available to measure and convert light beams to electrical signals. Such a camera has the sensitivity and dynamic range required to measure a BRDF range of $10^{-1}$ down to $10^{-5}$ $Sr^{-1}$, but its cost is prohibitive ($30k) In the preferred embodiment, however, the present invention uses a CID anti-blooming camera 130 (which is an order of magnitude lower in cost) to collect the data in a unique process involving collecting the data range segments (see software description for details). The scatter range segment and number of segments needed to reconstruct the data is determined by the particular CID camera specifications. The superior anti-blooming characteristics of the CID camera allows pixels to be saturated without affecting neighboring pixels. This tolerance is required in the unique reconstruction algorithm used in the present invention in which, during the data acquisition process, portions of the image are allowed to saturate in sequentially collected range segments.

The appropriate laser power and camera features of variable time integration and anti-blooming allow the desired data to be collected in less than a second. As stated above, a standard fiber optic acts as a face plate interface between the small end of the fiber optic bundle and the front end of the detector array.

A working example of a CID camera 130 is Model CIDTEC 2250 made by CIDTEC. This camera provides 512 pixels by 512 pixels resolution which provides 0.125 degrees angular resolution. Each pixel is a 15 um×15 um square. The camera is impervious to magnetic fields, shock, and vibration and does not degrade in sensitivity over time. Included in the capability of the camera is asynchronous full-frame capture and multiple frame integration. The camera power supply allows full control of camera speed and integration time.

4. Enclosure & Adjustments a. Housing And Mounting Plate

Figure 14:
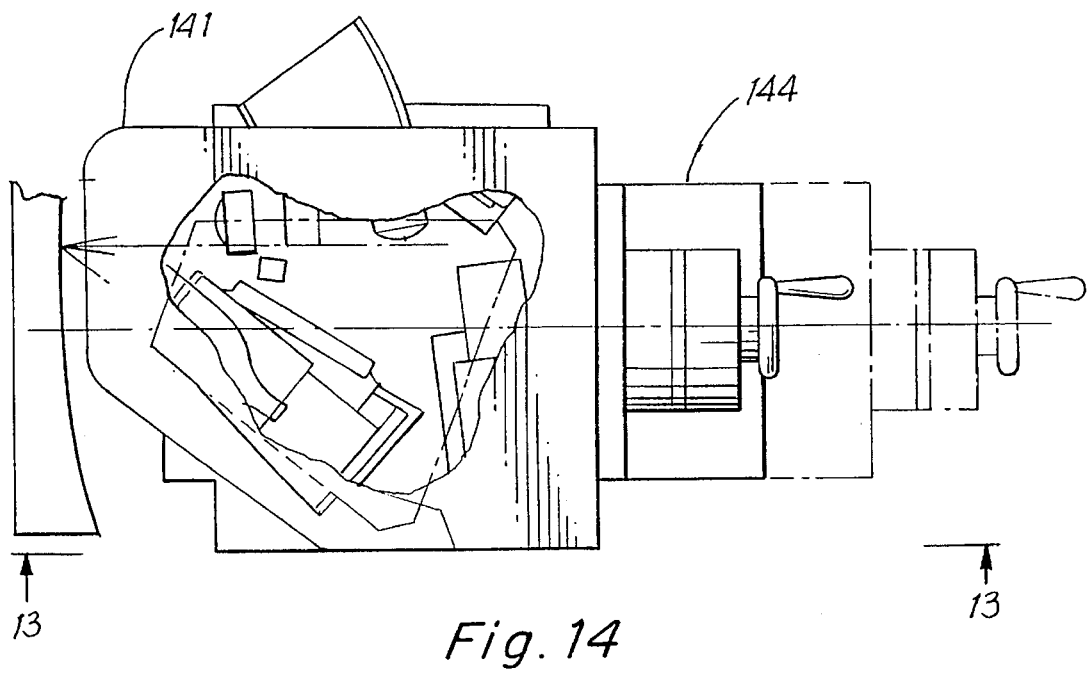
FIG. 14 is a top plan view in partial section of the measurement head showing the Z-stage alignment adjustment mechanism.
Figure 15:
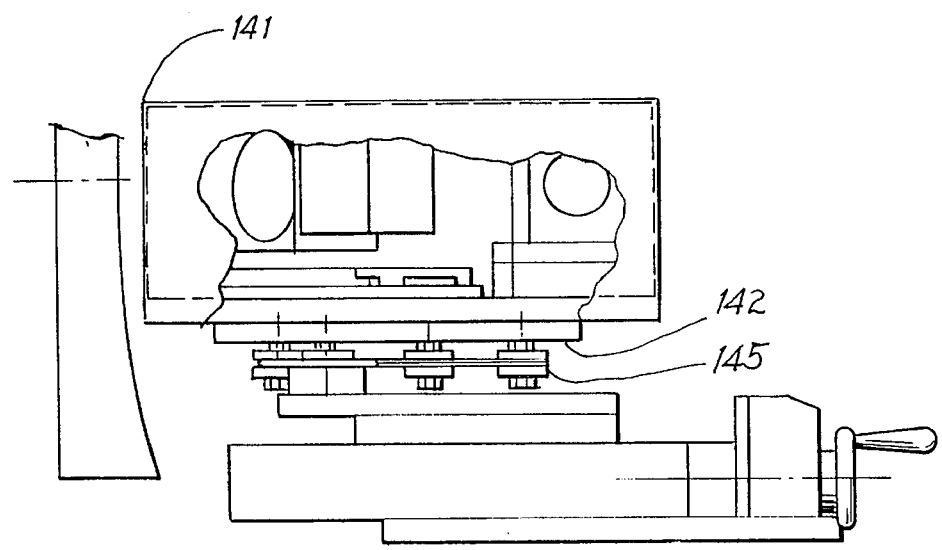
FIG. 15 is a side elevational view in partial section of the measurement head shown in FIG. 14 showing the azimuth alignment adjustment mechanism.

As shown in FIGS. 14 and 15, a strong, anodized, aluminum housing 141 is used to house all of the optics and electronics (except the computer). The measurement head housing 141 sits on top of a base mounting plate 142 or platform which is adapted for mounting onto a production line machine (not shown) and which contains the adjustment mechanisms required to perform the alignment procedure. These adjustments will include an axial position control 144 and an azimuth rotation control 145.

A working example is as follows:

The actual size of the measurement unit housing 141 is 11.50" long×9.125" wide×5.25" high, including the base mounting plate 142 and adjustment mechanisms 144, 145.

With the adjustment stages in operating position, the dimensions are 16.00" long×11.00" wide×9.50 high. With the adjustment stages fully extended, the dimensions are 22.00" long×11.00" wide×9.50" high.

b. Compactness of Measurement Head

The measurement head 10 (FIG. 1) itself is 9.5" long×8.5" wide×4.0" thick and contains the laser source 21, source optics 20, collection optics 30, and detector. These subsystems are integrated into a robust aluminum housing which is designed to withstand vibrations and G loads of harsh working environments. The measurement head 10 is a fully integrated unit that may also be hermetically sealed as described below. The adjustments required for sample to measurement head alignment require about 2–3 inches additional height.

c. Protective Shutter

The unit comes with a protective shutter 143 (FIG. 1), which is manually operated in the base instrument. This function may be automated as an optional feature. The shutter protects the internal optics from outside contaminants, especially when lubricants or other contaminants are present. If the shutter 143 is open and the sample under test is in harsh environments, applicant recommends precautions be made so that contaminants do not get onto the optics.

Alternatively a permanent window may be substituted for the shutter 143 to protect the collection optics which makes the measurement head a hermetically sealed unit. If a window is used, the measurement head 10 could actually be hermetically sealed and would become robust in the presence of cutting oils and other contaminates. However, the effects of such contaminants will strongly affect the measurements, particularly when sprayed onto the window.

d. Ruggedness Of The Measurement Head

The measurement head 10 contains very few individual parts; these include the beam dump 31, diode head 21, source focus lens 26, fused fiber bundle 40, collection lens 77, optical filter 120, and camera 130. These are mounted using vibration resistent mounts. Based on 0.5" aluminum, the measurement head will be built to withstand the vibrations of 0.2 g and 5 khz. The only moving part inside of the measurement head is a focus control 29. Thus the lifetime of the instrument is exceedingly long, and it will require little or no maintenance other than occasional cleaning (environment dependent). The ruggedness is also highly desirable for many of the market environments anticipated for the instrument's use (factory floor, aircraft, etc.).

IV. ALIGNMENT

A. Internal Alignment

The internal alignment of the scatterometer head is fairly simple. Internal alignment is required during assembly only, and is not required during use. The internal alignment of the measurement head is inherently defined by the mechanics of the system. Each of the subassemblies has sufficient individual alignment control.

The source optics, including the laser diode 21 with heat sink, the fold mirror 24 mount, the pseudo-depolarizer 25 mount and the focus lens 26 mount may be provided with their own internal tip and tilt adjustments relative to the collection optics. In this case, the internal alignment procedure is very simple. The collection optics 30 will be oriented within the measurement head 10. A kinematically mounted reference sample 146 (FIG. 19) will be used to define the desired test sample location. The source subassembly is first internally aligned to the reference sample 146 and beam dump 31.

B. External Alignment

Figure 3:
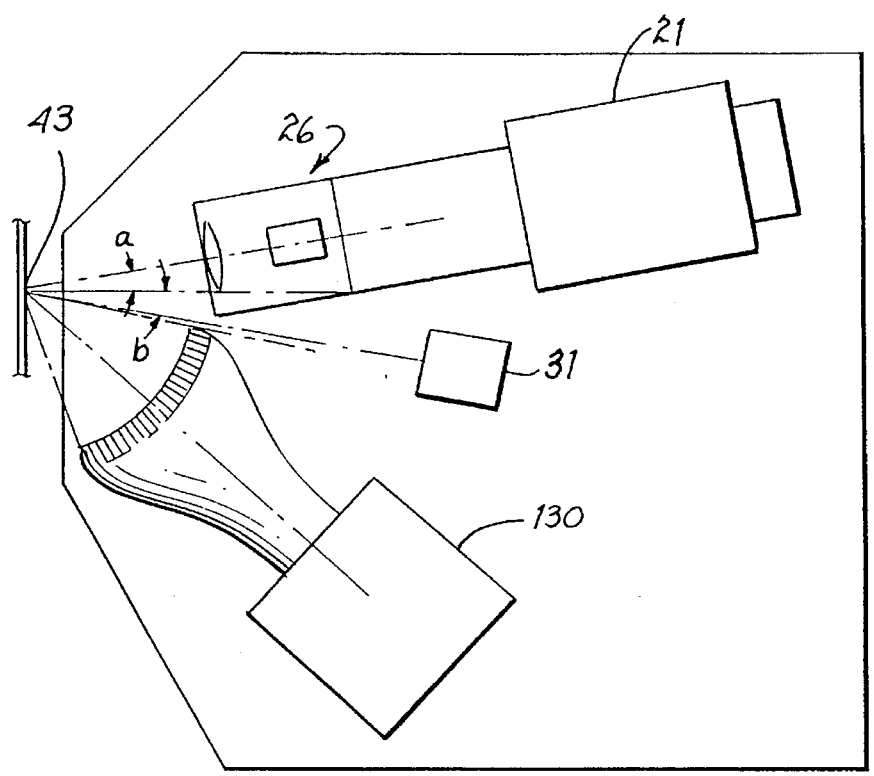
FIG. 3 is a schematic top plan view of the interior of the housing showing the measurement head containing the laser source, collection optics, beam dump and fiber optic/camera assembly.

The external alignment of the scatterometer to the part under test, or conversely, the alignment of the part under test to the scatterometer, is very simple. The alignment procedure is a two step process performed while watching a video screen. The user first controls the axial position (z-translation) of the part relative to the instrument and then controls the azimuth (which sets the incidence angle of the measurement head normal to the surface being measured) of the instrument relative to the point under test. Only a small azimuth adjustment (<10°) is required. (FIG. 3 shows a=b= 7°) Future expansion and automation of this adjustment may be developed to perform surface scans.

Axial Adjustment: The axial position of the measurement head 10 is adjusted to maintain a specified distance from the test sample. Once this is done, use the angular control 147 (FIG. 1) to bring the specular beam from the laser into the fiber optic bundle for the following two adjustments.

Rotational Adjustment: After the axial alignment is performed, the azimuth lock 148 is unlocked (FIG. 1) and the measurement head 10 is rotated until the specular reflection of the laser source is aligned to and blocked by the beam dump 31. Again, this alignment is made while watching the video monitor 161 until the specular reflection appears at a specific location on the monitor and takes only a few seconds.

Focus Adjustment: After rotational adjustment the focus control 29 (FIG. 1) is used to compensate for powered optics by getting the spot on the monitor as small as possible. The collection optics are then again moved to the measurement position by using angular control 147.

V. DATA ACQUISITION HARDWARE AND SOFTWARE

The software section of the detailed description is divided into several sections which include computer hardware interface, software user interface, data acquisition and reconstruction, data display, data analysis, data storage, two dimensional plotting, three dimensional plotting, graphical output and measurement speed.

A. Computer Hardware Interface

A computer system 150 is used as the measurement controller. The computer-scatterometer data acquisition system is shown schematically in FIG. 16. The computer interface allows for complete automation of the data acquisition process, such as laser power control, camera integration time, ambient light monitoring, and data capture. The automation provides consistency between measurements and reduces chances for human error. Also, the hardware eases labor intensive tasks such as focusing and diagnostic checking by providing real time video and status information. In addition, the features of the fiber bundle are fully utilized to provide a set of powerful capabilities such as realtime video monitoring, higher density measurements 0.125° or greater and measuring a large portion of the scatter hemisphere. These state-of-art capabilities use low cost readily available hardware. The design of the acquisition system has no moving parts, yet acquires large amounts of data in less than a second.

The recommended computer is a 486 compatible PC 148 which has the capability to interface to all of the scatterometer components and requires one IEEE-488 card 149 for diode monitoring and a TTL card 160 for high speed diode modulation.

A working example of a PC computer system is as follows:

Gateway 486DX2, 50 MHz/SMB for
high speed display of data, and
high speed pulse modulation of laser
640KB of RAM memory is sufficient for 50 sets of in-plane measurements without storage to disk. Hemispherical data requires storage to disk for each data set.

1.2 MB Floppy 1.44 MB 3.5" floppy for data transfer

MS-DOS 5.0

Windows 3.1

200 MB Hard Drive for mass data storage

VGA Graphics 800×600×256 for graphics display of data

Multisync Monitor

Frame Grabber to capture the video data from the camera

IEEE-488 Card & cable for data transfer to/from the laser power supply

TTL Digital Interface Card & cable for high speed pulse modulation of laser

Hybrid Data Acquisition/Control & Analysis Software

Abaton Laser Printer (optional)

Print-A-Plot HPGL Laser converter (optional)

The software and hardware developed will be compatible with 286/386 systems. However, the data display rate on these systems may take more than one second.

B. Software User Interface

The user interface will be a Graphical User Interface (GUI) with the look and feel of Windows 3.0, but will not require Windows 3.0. High speed graphics will be used to display information on the screen in near real time (less than 2 seconds). Data entry will be by keyboard 153 and mouse 154. Graphical Icons, axis scales, slide bars, push buttons, data entry windows with realtime error checking, and drop down menus will be used to provide intuitive and flexible interaction with the acquisition and data visualization process.

C. Data Acquisition and Data Reconstruction

As shown in FIG. 16 the acquisition system is composed of laser diode 21 and controller 155, a fiber optic/CID camera assembly 110 and controller 132, a 486 personal computer 148 and software. As far as the user is concerned, the measurement process consists of entering measurement parameters and then initiating the measurement sequence. The automatic measurement process consists of an ambient light test, scatter measurement, and data reconstruction. Once the data has been reconstructed it is displayed in the format previously specified by the user. The measurement and display process can be repeated once, a specified number of times, or continuously at a user selected interval (three seconds and up). After the data is collected it can be analyzed and stored. Detailed descriptions of these functions are in the following subsections.

1. Ambient Light Compensation

After all parameters have been selected by the user and before each and every scatter measurement the ambient light level will be measured. This measurement (laser off) will be continuous with a warning light on the computer screen until either the user aborts or the light level is dropped below an acceptable level. If the ambient measurement is terminated due to the light level being dropped to an acceptable level the scatter measurement will commence. If the ambient level is initially in the acceptable range, then the ambient and scatter measurements will both be accomplished in less than one second. Any mean ambient light within the acceptable threshold will automatically be subtracted out of the data.

2. Scatter Measurement/Data Acquisition

A camera and frame grabber which digitizes the video image will be used to collect the data. To collect data beyond the range of the camera, applicant has developed a unique algorithm to place multiple orders of magnitude of data one per frame (camera limit) in separate memory pages or frames on the frame grabber. The first page (frame) to be acquired has the power ($\phi_1$) and time ($t_1$) adjusted such that no pixels of the image are saturated. Each of the successive pages (frames) have the laser power incremented by an order of magnitude. Eventually some pixels close to the specular beam will saturate (without damage). This saturation is detectable and ignored since the relevant measurements for the saturated pixels were saved on a previous page (frame) when they were not saturated. The camera is anti-blooming, so saturating pixels do not offset neighboring pixels.

Figure 17:
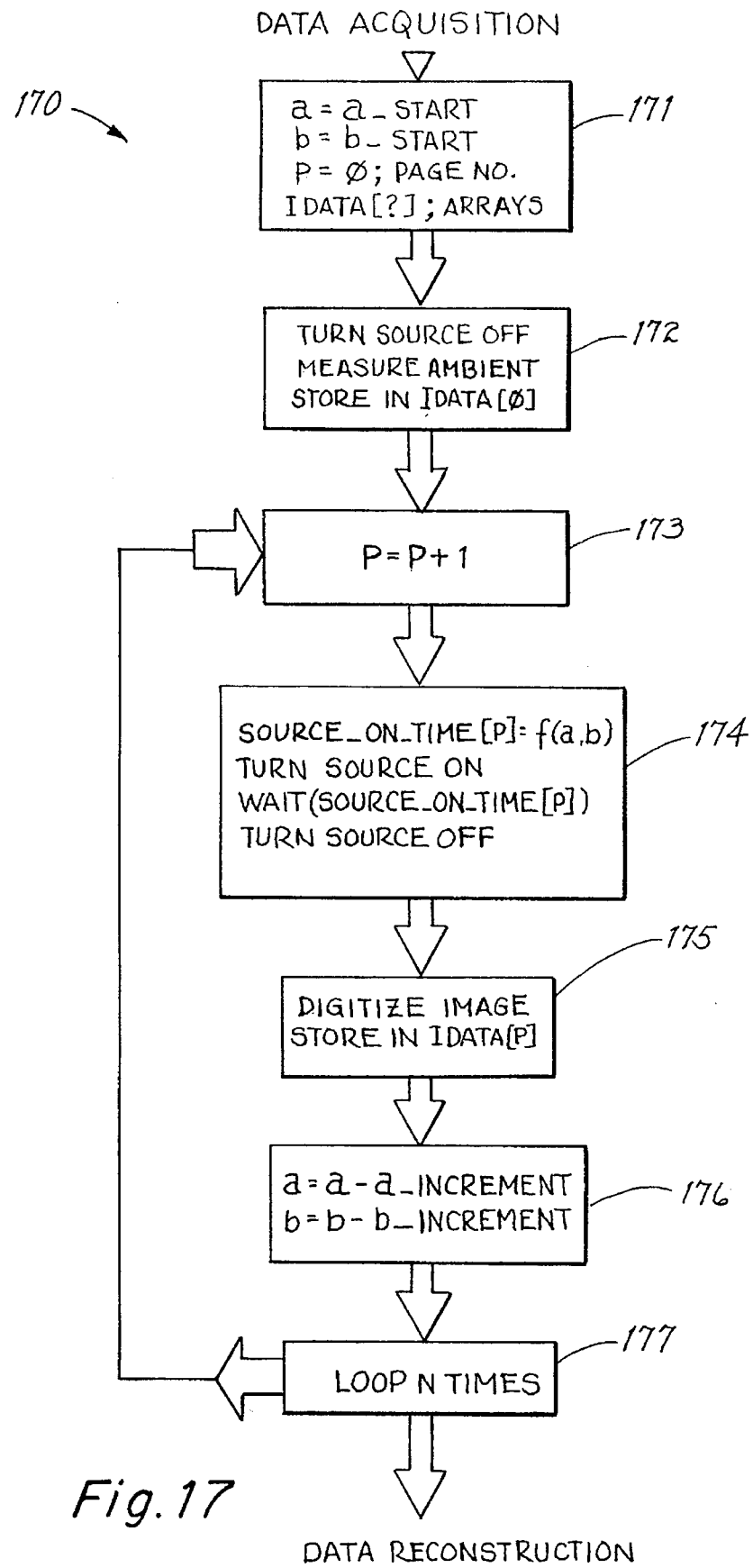
FIG. 17 is a flow chart showing the algorithm for the data acquisition process of the present invention.

The detailed data acquisition process 170 steps shown in FIG. 17 are described as follows (variables are in italics):

| Step | Description |
|---|---|
| 1. | Set variables a, b and p to start levels 171, where a and b represent predetermined exponential powers (for example, powers of ten) of on time of the laser as a function of a, b and p as follows: source-on-time = $t = t_1 \times 10^{(p-1)(a-b)}$ where $t_1$ is the initial time for page 1 such that no pixels are saturated given the laser power and p represents page number of the frame-grabber. As a working example, set a = −2; b = −1; page = 0; |
| 2. | With the laser off measure ambient light and store in the first page of the frame grabber 172. (Page = 0). |
| 3. | increment 173 page = page + 1. |
| 4. | Turn the laser on for sufficient time for the camera to collect data between $10^a$ to $10^b$ in magnitude 174, and, then |
| 5. | Turn laser off 174. |
| 6. | Digitize image and store the data in the current page of the frame grabber 175. |
| 7. | Decrement variables a, b by 1 at 176, a = a − 1; b = b − 1; (I.e., increase the diode on time by a predetermined amount (for example, one order of magnitude) |
| 8. | Repeat steps 3 through 7 N times 177. |

3. Data Reconstruction

The frame grabber now has N+1 images (data magnitude range dependent) stored on it, one per frame (page). The first image contains the ambient light measurement, which is a factor common to all of the frames in the sequence, and which is subtracted out of all pages leaving the reduced values in the remaining pages which comprise the scatter measurement data otherwise unchanged. These remaining frames of data contain information such as saturation, data not yet detectable, and greylevel. From this information a single scatter image can be constructed that represents the scatter profile. During the reconstruction process this scatter profile is normalized (scaled) relative, to the varied incident power of the laser diode and relative to a systematic reference calibration measurement taken previously. Each frame can hold various pixel resolutions of information depending on the angular resolution chosen. Only the measurement range selected by the user will be processed. In this way the user can choose between less data at higher display speeds or high volume information at lower display rates.

Figure 18:
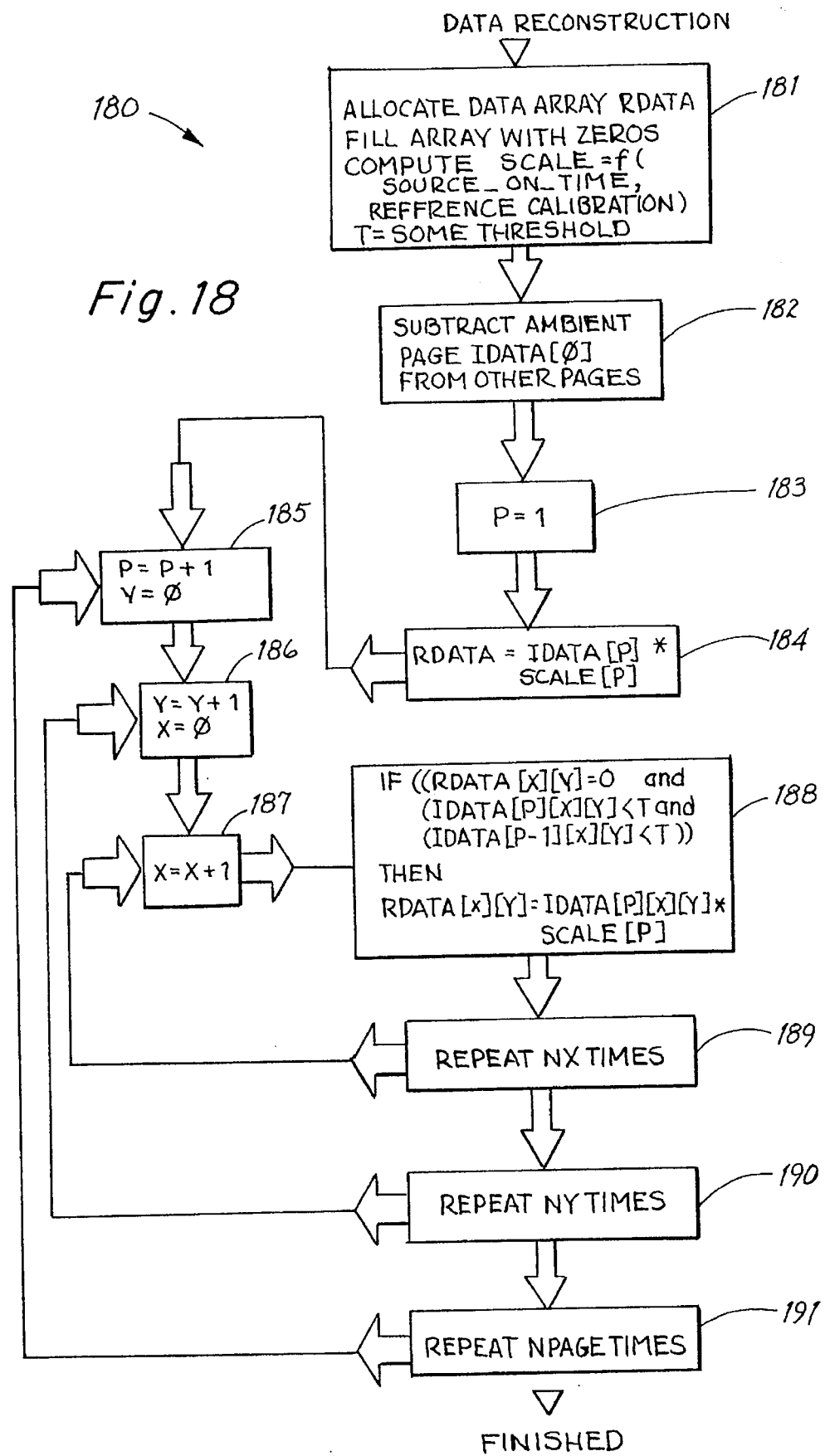
FIG. 18 is a flow chart showing the algorithm for the data reconstruction process of the present invention.

Once the N+1 data frames, i.e. one ambient reference frame and N data frames, have been collected, the detailed steps of the data reconstruction process 180 to reconstruct the scatter profile are shown in FIG. 18:

1. A profile array (RDATA) is set up in computer memory filled with zeros 181.
2. A dual function scale factor is computed. The scale factor is a function of the source on time of the laser diode and a function of the systematic reference calibration measurement. As seen below, preferably both scale factors are applied simultaneously during the reconstruction process thereby shortening the reconstruction time period. However, optionally, the systematic calibration scale factor may be applied after the reconstruction is first completed.
3. The ambient light (reference frame, page 0) is subtracted from the scatter data 182. This is assumed to be the same for all frames of scatter data since the camera integrated for the same time on each frame. It was the laser on-off time that changed.
4. Set variable p=1 at 183 and scale the data in the first data frame (page 1) and add the scaled data to the profile array RDATA at 184.
5. Scale and add the scatter data in the next succeeding data frame to the profile array according to the formula described below and shown graphically in FIG. 18 at 185–190. This is done on a pixel by pixel basis 185, 186, 187, 188, 189 and 190, and for each data frame in sequence 191, storing the pixel data only if the pixel data has not been stored previously 188. That is, the pixel data from the data frame is stored in its spot in the profile array only if the data already in that spot in the profile array is zero and the data in that spot in the current and any prior data frame is less than the saturation level of the pixel. The reason for this double test as to saturation level is to negate the effect of oversaturation of a pixel which causes the pixel to reverse color and look like it is not saturated. Looking to the prior frame to confirm the pixel was saturated prevents the frame grabber from being fooled by the pixel color reversal due to oversaturation. Thus, if pixels in the current frame or previous frame are saturated or any pixels in any previous frame (not the current page) are non-zero then the pixel has been stored previously 188 and data in the current frame is ignored. Thus, data gets added to an x-y location in the profile array only once in the entire reconstruction process. If pixels in the profile array are still zero, it means the scatter was too low to measure.
6. Step 5 is repeated for all frames until all frames 191, 185 have been processed.

Now that the scatter profile has been constructed it can be displayed and/or stored to disk.

D. Data Display

Figure 20:
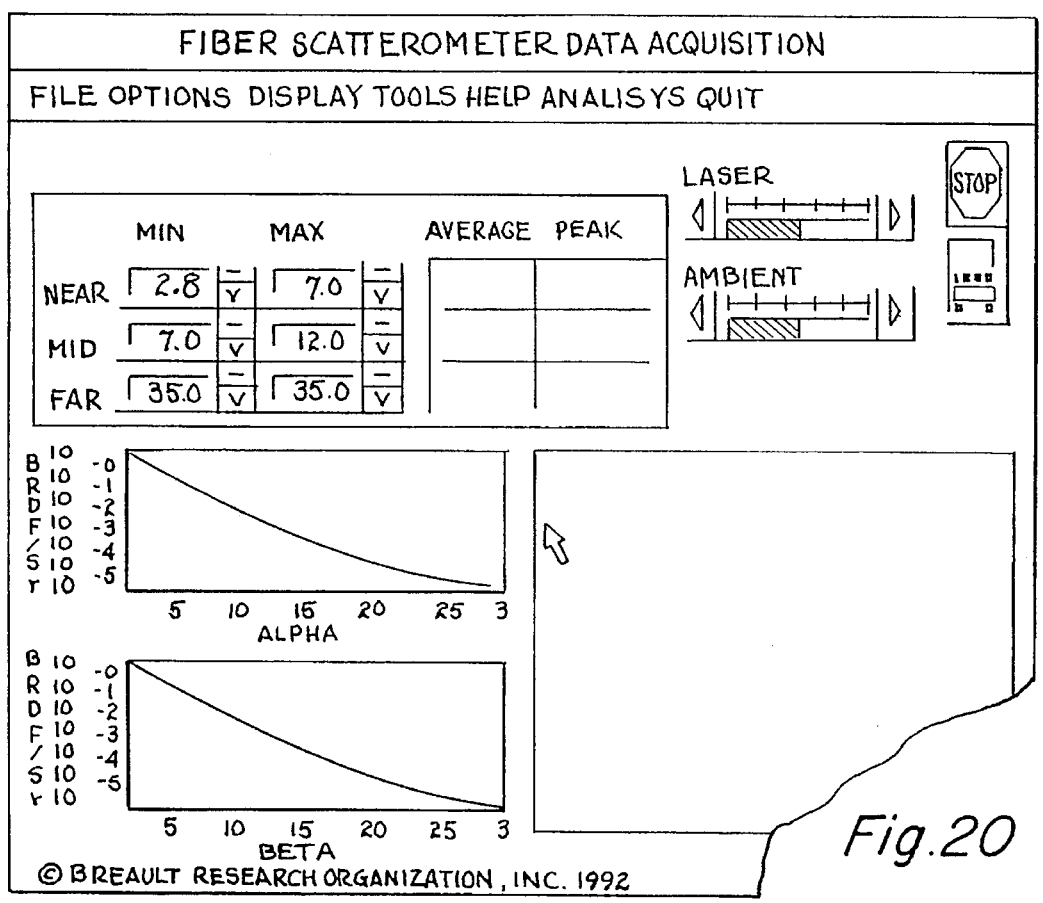
FIG. 20 is the computer screen showing the format for presenting the analyzed data.
Figure 21:
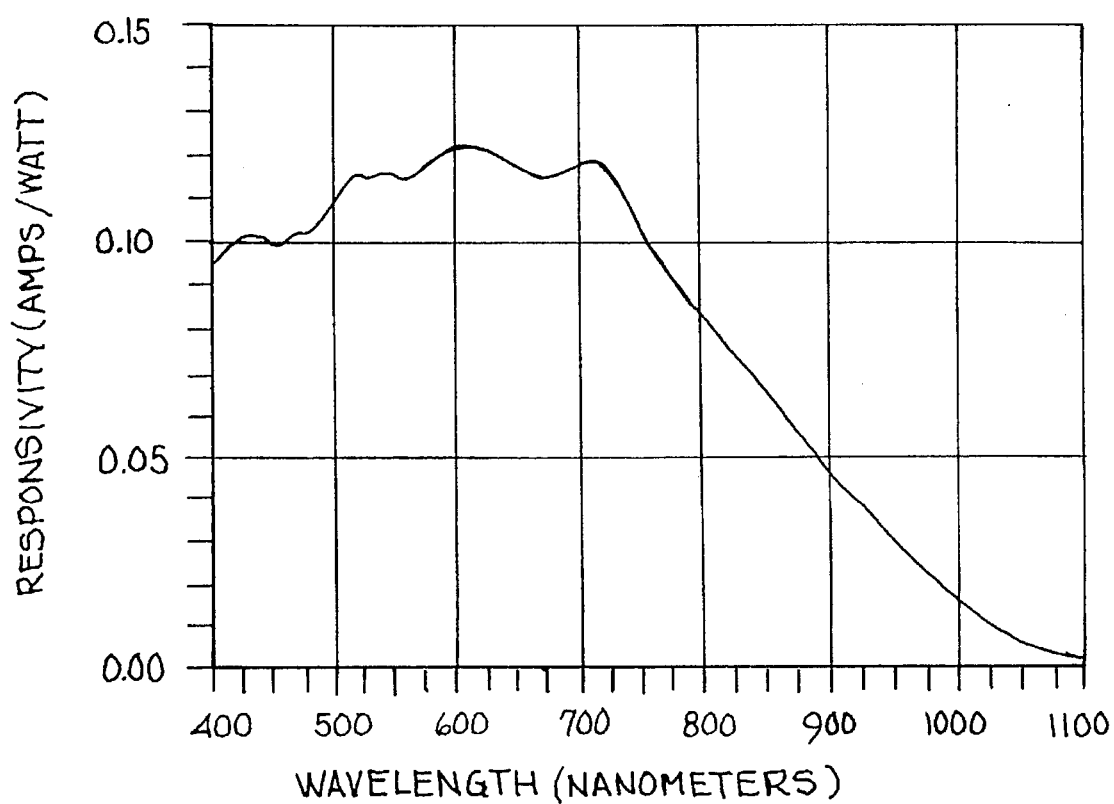
FIG. 21 is a spectral response curve for a CID camera of the present invention.

The latest GUI technology, and high speed graphics are used to visualize the data as shown in the graphical output screen 193 in FIG. 20. Using graphical slide bars the user is able to select multiple segments (near, mid, far angles) of the BRDF curve. The values over the range of a segment can then be reported by peak value and/or average value. These values can be displayed in one window while the data is plotted in multiple formats in another window. Other values that can be displayed are: diode output power, average ambient light level, RMS, PSD, TIS, and auto-correlation. Also the camera system provides real time display of large sections of the scatter hemisphere.

E. Data Analysis

1. Normalization

The data is normalized to the laser output power. This factor is reflected in the scale factor in block 181 of FIG. 18.

The diode controller 155 has a photodiode feedback circuit (not shown) that stabilizes the output power of the laser. This circuit can be sampled to read out the power output from the laser. The diode responsivity (milliamps/milliwatt) is a fixed known characteristic of the laser diode calibrated by the manufacturer. The photo diode current is read automatically through the IEEE-488 bus during the scatter measurement and is used to calculate the laser power.

2. Calibration

Figure 19:
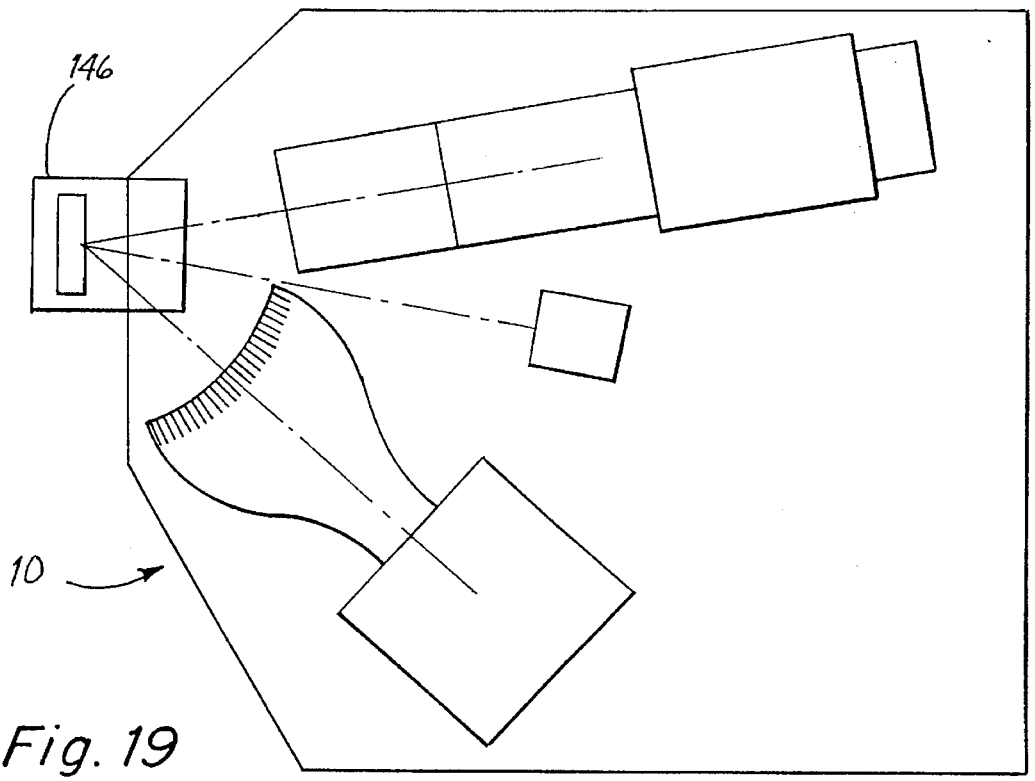
FIG. 19 is a schematic tap plan view of the measurement layout for calibration and system profile.

FIG. 19 shows a reference sample adapter plate 146 which easily snaps onto the front of the measurement head. This is used to calibrate scatter data using a NIST traceable Reference Standard. This factor is reflected in the scaling factor in block 181 of FIG. 18. If the data has not been normalized with respect to output power, it is recommended to use a reference measurement taken the same day as the measurement. This process maximizes accuracy of calibrated measurements, and minimizes error due to any possible power changes from one measurement to another. To eliminate this possible error the software may be put into an automatic mode where the sample and reference data are always normalized with respect to the output power which is measured and stored with each data set.

3. System Profile

The system profile is used to determine how close to specular measurements are valid. It also determines the lowest BRDF the instrument can detect. When the two measurements, system profile versus scatter measurement, are overlaid on a graph, any scatter data that overlaps the system profile should be considered to be invalid.

A kinematically mounted reference sample consisting of a highly polished mirror is provided to allow measurement of the system profile. This configuration is preferred because of the potential interaction of stray light from the face of the fiber shell and the sample surface. Since reference samples are available that are significantly better in rms surface finish than most samples to be measured, this method of determining the system profile is sufficient.

4. Volume of Information

If all the data collected by a 512×512 camera were used, the image and data file would be over 256KB when stored in binary. The user can specify what region and resolution of the scatter hemisphere that is to be collected, analyzed, and stored. This region can range from a single plane or a two dimensional segment of the scatter hemisphere. A 512×512 hemispherical measurement can be displayed under 10 seconds.

F. Data Storage

A resident or remote personal computer is preferred as the optimum controller. It allows data acquisition, analysis, and storage to be performed quickly and easily. In addition, software alterations to match increasing demands can be performed with less perturbations than using a micro-controller. Also large volumes of data can be stored on a hard disk or floppy depending their size.

Data can be accumulated in memory and later stored to disk. The amount of data stored in memory will depend on the data acquisition size. At a minimum for in-plane measurements with the minimum BRDF (2° in plane, 0.125° resolution), the number of data sets stored in memory will be fifty (50).

G. Two Dimensional Plotting

Conventional BRDF plotting software, such as SOFTSCAT-2D™ software package by BRO is available to plot all two-dimensional data taken by a scatterometer complying with the ASTM standard E1392-90. Also, the software can easily be configured to read other data formats.

The data will be computed and plotted in a variety of ways, including:

$\beta - \beta_o$ vs BSDF (Harvey Shack)

$\theta - \theta_o$ or $\theta$ vs BSDF $\theta$ vs BSDF polar plots

RMS surface roughness, RMS slope, and power spectral density linear, log-log, or semi-log format Some of SOFTSCAT-2D's features include:

ability to "zoom in" on the data cross-hair positioning user-definable legends multiplying and/or adding constants to the data (for comparing different curve shapes independent of magnitude)

H. Three Dimensional Plotting

Conventional software, such as, SOFTSCAT-3D, by BRO plots all three-dimensional data, such as, hemispherical data and surface scans taken by a scatterometer complying with the ASTM standard E1392-90. Also, the software can easily be configured to read other data formats.

The data can be plotted in a variety of ways, including:

color scaled perspective plots color maps contours cross-sectional plots of the three dimensional data Other features include:

cubic splines plotting the log of the data cross-hair positioning automatic labeling I. Graphic Output Both SOFTSCAT-2D and SOFTSCAT-3D support the following:

over 200 graphics cards

Epson printer output

HPGL plotter output

HPGL file output for input to word processors, such as, Word Perfect publication quality output

VI. ADDITIONAL MEASUREMENT TECHNIQUES

A. Rapid Surface Scan

Taking data at a few points on a test surface is not always adequate. There are times when an entire surface must be characterized. Very fast surface scans of a surface can be performed. Since the data is collected at near video rates, entire surfaces can be scanned very quickly. Instead of signal integration being the limiting factor, now the limitation is the speed of the x-y scanner.

Note that there are now four dimensions to the BRDF data which include x, y, $\alpha$, $\beta$, where $\alpha$ and $\beta$ are the hemispherical angles in cosine space. Now the data needs a 4th display parameter which can be supplied by displaying the data in rapid succession, much like a movie.

B. Processing and Surface Analysis

A two dimensional grey scale image is produced with the hemispherical approach. From the patterns in the image a wide range of image processing and data analysis software can be developed to analyze the nature of the surface and its defects.

A working example of a scatterometer of the present invention has the following features:

TABLE 1

MEASUREMENT HEAD COMPONENT CHARACTERISTICS:

| Item | Characteristics |
|---|---|
| Dimensions | 9.5 × 8.5 × 4" without adjustments |
| Shutter | Removable cover |
| Radiation Source | Laser Diode, 70 mW, 830–840 nm collimated, circulated, wavefront corrected computer controlled with temperature & output stabilization |
| Polarization | Randomly polarized (Cornu pseudo-depolarizer) |
| Source Focus Lens & Control | Adjustable for powered optics |
| Fiber Bundle | Solid glass fiber bundle ≈5000 fibers across dia. ≈0.015° resolution/fiber 40–60° angular measurement range |
| Optical Filter | Bandpass filter to reduce ambient light |
| Beam Dump | Traps specular reflection from measurement surface |
| Camera Head | CID detector array 512 × 512 resolution 15 um × 15 um pixel size 11 mm diagonal array anti-blooming |

TABLE 2

SCATTEROMETER PARAMETERS

| Parameter | Range/Quantity |
|---|---|
| BRDF Range | $10^{-1}$ to $10^{-5}$ |
| Angular Resolution[1] | 0.25° (256 × 256) 0.125° (512 × 512) |
| Angular Range | 2° to ≈60° |
| Hemispherical Measurement | Forward Scatter 40°–60° hemispherical circular section |
| Wavelength | 830°–840° |
| Spot Size | ≈4 mm |
| Incident Angle | 7° |

[1]Angular resolution is selectable under computer control and is defined by the spatial resolution digitized from the camera.
Measurement Time <1 sec
Display Time <2 sec

TABLE 3

DATA ACQUISITION AND SOFTWARE

| Parameter | Description |
|---|---|
| User Interface | Graphical User Interface (GUI), keyboard, and mouse |
| Measurement | time <1 second, at least 3 second intervals BRDF Range $10^{-1}$ to $10^{-5}$ 0.125° or 0.25° resolution in-plane BRDF (2° to 40° minimum) hemispherical area (out-of-plane) |
| Display | computer screen display time <2 seconds video display in realtime, near, mid, and far angle BRDF (peak and/or average) |
| Analysis | normalization, calibration |

TABLE 3-continued

DATA ACQUISITION AND SOFTWARE

| Parameter | Description |
|---|---|
| Data Storage | TIS, RMS, PSD, AutoCorrelation, BRDF at other wavelengths Selectively stores data in the ASTM 1392-90& binary formats Hard disk storage |
| Graphical Output | All acquired data can be plotted in 2 or 3 dimensions Publication quality output |

VII. TECHNICAL NOTES AND CALCULATIONS

TECHNICAL NOTES

Detector Linearity

As mentioned in Section 4.3 the CID Camera will be allowed to saturate. From experiments at BRO the camera can take two orders of magnitude of power beyond saturation before the pixels begin to invert. This inversion, as described by the manufacturer, is due to the electronics subtracting out what it believes to be fixed pattern noise. This inversion has no effect on the final data since the saturation is detected well before the inversion, and the data was collected before the saturation. Treating the camera in this way is quite common in the laser profiling market. And completely safe for the camera when the laser power is kept within a reasonable range, which is wavelength dependent. The power used for the proposed instrument is orders of magnitude within the safety limit.

The laser output power can be controlled to within one (1) percent, through the use of a built in thermoelectric cooler and a feedback power control loop.

Calibration

The two methods of calibration which can be used for normalizing the BSDF data are the Reference Substitution Process method (RSS) and the Attenuated Input Beam Direct Measurement method (ABDM).

These methods are described in detail as follows:

RSS Calibration Method

Currently, BRO scatterometers can automatically calibrate the data by measuring a gold calibration standard (which is traceable to a NIST standard). A gold reference works well with the large spectral range required. The equations are:

$BRDF_S = [BRDF_R * \cos(\theta_R) * V_S] / [\cos(\theta_i) * \cos(\Phi_i) * V_R]$ $BRDF_R = P_R / \pi$ (Lambertian)

where:

$BRDF_S$=BRDF of the sample $BRDF_R$=BRDF of the reference standard $P_R$=reflectivity of the Lambertian reference (known)

$\theta_i, \Phi_i$=detector angles in and out of plane relative to the sample normal $\theta_R, \Phi_R$=detector angles in and out of plane when taking reference measurement $V_i$=voltage from sample scatter at $\theta_i$ and $\Phi_i$ $V_R$=voltage from reference scatter at $\theta_R$ and $\Phi_R$ ($\Phi_R$=zero degrees)

The errors in the RSS method are as follows:

Error in the measured reflectivity of the standard itself (constant).

The reference is measured at one detector angle (10 degrees from specular) with the assumption that the reference is diffuse and the BRDF curve is flat over a certain range of angles. In reality, there are no perfectly flat BRDF curves. Even from the most diffuse whites the BRDF can change ±30% or more.

The contribution of these errors is constant; this means that they alter the level of the BSDF curve and not the shape of the curve. An advantage to this method is that some errors, or other factors in the data acquisition process common to taking data from the standard and the test sample, are normalized out. Past data taken on three different BRO scatterometers at the customer site with the same sample (Martin Black) show this calibration technique gives consistent results when implemented correctly.

ABDM Calibration Method

The Absolute method uses a reference mirror to direct the incident beam directly into the detector, or to catch the beam with no sample or reference mirror in place. The equations are:

$BRDF_S V_S A_S R^2 / [V_T A_T * \cos(\theta_i) * \cos(\Phi_i) * a * T]$ where $\theta_i, \Phi_i$=detector angles in and out of plane relative to the sample normal Vs=voltage output when measuring the test sample $V_T$=voltage output when all radiation incident on sample enters the sample detector when measuring total power $A_T$=attenuation required to allow all power on detector (positive exponent)

a=aperture area $A_S$=attenuation at $\theta_S$, $\Phi_S$

R=distance from collecting optics to sample

T=reflectivity of the reference mirror (T=1.0, for the straight through method).

The errors in the ABDM method are as follows:

error in normalizing out attenuation which is wavelength dependent (constant)

error in measuring "R" and "a" which make up the solid angle error in determining that all the signal from the source is collected by the detector, and no significant additional stray light is present.

linearity of the sample and reference detectors, even when the attenuators are in place For the laser sources, the RSS calibration method cited above will be used.

Stray Light Control

There are two sources of stray radiation in any scatterometer: the instrument profile, and the illumination beam. The instrument profile is a fixed noise produced by the interaction between the forward scatter from the illumination optics (chiefly the last optic before the sample) and the collection system's field-of-view. Its primary effect is to limit one's ability to make near-specular measurements. However, this is only a limitation when testing specular samples. When testing diffuse samples, the instrument profile is generally not a problem.

There are two ways to reduce the instrument profile: decrease the source size or beam diameter, or decrease the collecting optic's field-of-view. Adjusting the source size or beam diameter changes the illuminated spot size on the primary mirror. A smaller collector FOV reduces the angle at which that spot is seen by the detector. The BRO scatterometers optimize these parameters in order to achieve an optimum spot size and a small instrument profile.

The other source of stray light is the reflected beam. This arises when the beam strikes walls or support structures. If there are no walls, this source of stray light from internal sources is reduced. To avoid stray light from the support structure, it is best to underfill the sample. However, this is not always possible. In the "over-illumination" case, the beam spills off the sample onto the surrounding support structure. To minimize stray radiation from the support structure, a special sample holder has been designed. By eliminating most of the holder structure around the sample, controlling the overillumination beam size (focus adjust), and using beam dumps, BRO has been able to minimize all the instrument sources of stray light.

CALCULATIONS

The CID camera chosen has a full well capacity of 450,000 electrons, which is the saturation point. Thus the objective is when the BRDF is at lowest required to measure ($10^{-5}$) it is desired that a pixel element accumulate on the order of 250,000 to 450,000 electrons. For a safety factor a goal of 450,000 electrons is assumed.

At the minimum $BRDF_{min}$ the signal in electrons on the camera will be, $$N = \frac{\phi_i \cdot t \cdot R \cdot BRDF_{min} \cdot \Omega \cdot \gamma}{q}$$

where:

t=frame (integration time) [sec]

$\phi_i$=input laser power [watts]

$BRDF_{min} = 10^{-5}$ [steradians$^{-1}$]

$\Omega$=solid angle [steradians]

$\gamma$=throughput ratio of the fiber

R=detector responsivity [amps/watts]

q=charge of electron 1.6 E-19 [coulombs]

N=number of collected electrons

From among commercially available laser diodes two choices are made, at different locations in the available spectrum. Substituting representative values for these wavelengths:

t=0.200 sec

BRDF=1×10$^{.15}$ $\Omega = (0.25/57.3)^2$ $\gamma = 0.4$ q=1.6E-19

$\phi_i$(840)=70 mw $\phi_i$(670)=3 mw

R (840)=0.065 amps/watts

R (670)=0.115 amps/watts 1 amp=0.6 E$^{19}$ electron/sec

From the CID responsivity curve shown below, it is seen that the camera sensitivity peaks around 600 nm, while commercialized diodes have more power at higher wavelengths.

Thus, from the above the product $\phi_i \cdot R$ must be maximized.

$\lambda = 670$ nm or $\quad \lambda = 840$ nm
$q_i = 3$ mW $\quad\quad q_i = 70$ mW From the CID responsivity curve shown the responsivities at these wavelengths are:

$R = f(\lambda$ nm$)$
$R(670) = 0.115$ Amps/Watt
$R(840) = 0.065$ Amps/Watt
using the above equation and values we get
$N(670) = 32844$ electrons
$N(840) = 433160$ electrons Previously it was assumed that $4.5 \times 10^5$ electrons were desired. Thus, the 670 nm diode is not sufficient but, the 840 nm 70 mW is enough. Thus diode power can be controlled from a few micro-watts to 70 mW by controlling the diode on-off time (down to 10 ns, through the use of the diode controller).

The foregoing description of a preferred embodiment and best mode of the invention known to applicant at the time of filing the application has been presented for the purposes of illustration and description. It is not intended to be exhaustive or to limit the invention to the precise form disclosed, and obviously many modifications and variations are possible in the light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. An apparatus for collecting light from a common light source which comprises:

a plurality of individual fiber optic elements one end of each of which is fixed in spaced relation to each other and an other end of each of which is arranged in an indexed array, the plurality of fiber optic elements have a common field of view and a face at the one end of each of which is fixed in a curved surface having a radius of curvature such that the longitudinal axis of each fiber optic element at the one end substantially converges at the common light source which, with respect to each fiber optic element, radiates light normal to a plane which is both tangent to the face of the fiber optic element at the normal axis and perpendicular to the longitudinal axis of the fiber optic element, whereby the light radiating angularly from the light source is received simultaneously at the one end by each fiber optic element and is transmitted to the other end.

2. The apparatus as recited in claim 1, wherein the curved surface is a full hemisphere.

3. The apparatus, as recited in claim 2, further comprising:

a rigid hemi-dome which has a plurality of openings in each one of which is secured one end of one of the fiber optic elements.

4. The apparatus, as recited in claim 2, wherein the plurality of fiber optic elements form a tapered bundle.

5. The apparatus, as recited in claim 4, wherein the tapered bundle is fused.

6. The apparatus, as recited in claim 1, wherein the curved surface is a spherical segment.

7. The apparatus, as recited in claim 6, wherein the plurality of fiber optic elements is a tapered fiber optic bundle, and the spherical surface is in the tapered portion of the bundle.

8. The apparatus, as recited in claim 7, wherein the curved surface is in the one end which is a wide end of the bundle and the other end is a narrow end of the bundle.

9. The apparatus, as recited in claim 7, wherein the tapered fiber optic bundle is a unitary bundle which has a wide central portion, a first tapered portion in which the spherical surface is located at the one end and a second tapered portion which terminates at the other end, the first and second tapered portions being tapered in opposite directions.

10. The apparatus, as recited in claim 9, wherein the bundle is fused.

11. The apparatus, as recited in claim 9, wherein the first and second tapered portions each terminate at wide ends which are bonded together to form the wide central portion.

12. The apparatus, as recited in claim 11, wherein the first and second tapered portions are rotated 45° relative to each other prior to being bonded.

13. The apparatus, as recited in claim 9, wherein the unitary bundle is a double tapered fused fiber optic bundle.

14. The apparatus, as recited in claim 13, wherein the light source is a point on a surface to be tested and further comprising:

a path cut through the bundle for transmitting therethrough light from a remote light source to illuminate the point.

15. The apparatus, as recited in claim 14, further comprising:

means to suppress a specular beam reflected from the point.

16. The apparatus as recited in claim 7, further comprising:

the bundle having an upper portion, a longitudinal slot in the upper portion of the bundle for input of a source beam of various angles of incidence.

17. The apparatus, as recited in claim 1, wherein the curved surface is a segment fixing the one ends of all the fiber optic elements in a common plane containing their longitudinal axis.

18. The apparatus, as recited in claim 17, further comprising:

an aperture block which has a plurality of radial spaced passages in each one of which is secured one fiber optic element.

19. The apparatus, as recited in claim 1, further comprising:

the fiber optic elements are a bundle and a narrow band coating is on the outside of the fiber bundle.

20. The apparatus of claim 1 wherein the other end is flat.

21. A method of manufacturing a fiber optic bundle comprising the steps of:

a) forming a tapered fiber optic bundle, and b) cutting a concave face in the tapered portion of the bundle such that for each fiber in the bundle a plane tangent to the face at the normal axis to the fiber is also perpendicular to the longitudinal axis of the fiber.

* * * * *